United States Patent
Nagamizu

(10) Patent No.: US 11,253,138 B2
(45) Date of Patent: Feb. 22, 2022

(54) ENDOSCOPIC APPARATUS

(71) Applicant: Olympus Corporation, Hachioji (JP)

(72) Inventor: Hiroyuki Nagamizu, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 435 days.

(21) Appl. No.: 16/214,205

(22) Filed: Dec. 10, 2018

(65) Prior Publication Data

US 2019/0110664 A1 Apr. 18, 2019

Related U.S. Application Data

(63) Continuation of application No. PCT/JP2017/007831, filed on Feb. 28, 2017.

(30) Foreign Application Priority Data

Jun. 17, 2016 (JP) .............................. JP2016-120540

(51) Int. Cl.
*A61B 1/00* (2006.01)
*G02B 23/24* (2006.01)
(Continued)

(52) U.S. Cl.
CPC ...... *A61B 1/00124* (2013.01); *A61B 1/00009* (2013.01); *A61B 1/00096* (2013.01);
(Continued)

(58) Field of Classification Search
CPC . A61B 1/0055; A61B 1/0124; A61B 1/00009; A61B 1/00114; A61B 1/04;
(Continued)

(56) References Cited

U.S. PATENT DOCUMENTS

2009/0177038 A1 7/2009 Yashiro et al.
2013/0027534 A1* 1/2013 Kibayashi ............... G02B 7/10
348/65
(Continued)

FOREIGN PATENT DOCUMENTS

JP 1994130305 * 5/1994 ............... A61B 1/04
JP 10-014868 1/1998
(Continued)

OTHER PUBLICATIONS

JP-1994130305, May 1994, Yoshimitsu Koichi, Figures of japanese patent (Year: 1994).*
(Continued)

*Primary Examiner* — Alexandra L Newton
(74) *Attorney, Agent, or Firm* — Scully, Scott, Murphy & Presser, P.C.

(57) ABSTRACT

The disclosed technology is directed to an endoscopic apparatus comprises an endoscope having a cable connected to an electronic circuit part of the endoscope. The cable includes an elongated covering and an elongated component configured to be concentrically engaged with the elongated covering. A securing member is used to bind and to secure the elongated covering and the elongated component to one another. The elongated covering includes at least one recess formed on an outer circumferential area of the elongated covering on which the securing member binds and secures the elongated covering. The securing member has a portion that sinks in the at least one recess and secures the elongated covering and the elongated component that is exposed through the at least one recess.

16 Claims, 22 Drawing Sheets

(51) Int. Cl.
*A61B 1/05* (2006.01)
*A61B 1/04* (2006.01)
(52) U.S. Cl.
CPC ............ *A61B 1/00114* (2013.01); *A61B 1/04* (2013.01); *A61B 1/051* (2013.01); *G02B 23/24* (2013.01)
(58) Field of Classification Search
CPC ............ A61B 2562/187; H01R 4/2445; H01R 9/2416; H01L 2224/42; H01L 2224/47
See application file for complete search history.

(56) References Cited

U.S. PATENT DOCUMENTS

2013/0050457 A1* 2/2013 Murayama ........... A61B 1/0008
348/75
2014/0326857 A1* 11/2014 Sekido ............. H01L 27/14636
250/208.1

FOREIGN PATENT DOCUMENTS

| JP | 10-033474 | 2/1998 |
| JP | 11-019035 | 1/1999 |
| JP | 2007-007179 | 1/2007 |
| JP | 2009-153902 | 7/2009 |
| JP | 2010-069186 | 4/2010 |
| JP | 2012-205808 | 10/2012 |
| JP | 2015-062555 | 4/2015 |

OTHER PUBLICATIONS

International Search Report and Written Opinion from corresponding International Application No. PCT/JP2017/007831, dated May 23, 2017.

* cited by examiner

FIG. 2

ENDOSCOPIC APPARATUS

CROSS-REFERENCE TO RELATED APPLICATIONS

This application is a continuation application of PCT Application No. PCT/JP2017/007831 filed on Feb. 28, 2017, which in turn claim priority to the Japanese Patent Application No. 2016-120540 filed on Jun. 17, 2016 in Japan which is hereby incorporated by reference in its entirety.

TECHNICAL FIELD

The present disclosure relates to an endoscopic apparatus in which in the vicinity of a joint portion of a cable that is connected to an electronic circuit part and a circuit board of an endoscope, a component of the cable and a covering that covers the component are secured to each other.

DESCRIPTION OF THE RELATED ART

Endoscopes are widely used in the industrial and medical fields. Particularly, a medical endoscope, for example, that has an image capturing portion disposed in the distal end of a slender insertion portion thereof allows the user to observe, on a monitor, an image captured of an examined region in a body cavity by the image capturing unit when the insertion portion is inserted into the body cavity.

The image capturing portion disposed in the distal end of the insertion portion of the endoscope is constructed as a unit in which a circuit board is connected to a solid-state image capturing device such as a CCD (charge coupled device), a CMOS (complementary metal-oxide-semiconductor), or the like. The image capturing portion is supplied with a power supply signal, a drive signal, etc. from a signal processor in a subsequent stage through a cable connected to the circuit board. The image capturing portion delivers an output signal representing a captured image of a subject through the cable to the signal processor in the subsequent stage. When the cable is pulled in the direction of a proximal end thereof upon bending of the insertion portion, the covering of the cable tends to be retracted toward a proximal-end side with respect to a component of the cable, with the result that the component of the cable may be exposed, possibly resulting in a contact failure in a joint portion connected to the circuit board and a break-off of leads. Therefore, it is necessary to secure the component of the cable and the covering of the cable to each other in the vicinity of the joint portion between an electronic circuit part and the circuit board.

To meet the demand, Japanese Patent Laid-Open No. Hei 10-33474, for example, discloses a technology in which a signal line covered with a covering is connected by soldering to a flexible board, and thereafter the signal line and the covering are bound by a thread to a concave portion of an extension of the flexible board, thereby providing a thread-wound secured portion by which the extension and the covering over the signal line are secured to each other. The flexible board is coated in its entirety, including a soldered region of the signal line and the thread-wound secured portion of the signal line, with an adhesive and covered with a heat-shrinkable tube.

However, the conventional thread-wound securing structure disclosed in Japanese Patent Laid-Open No. Hei 10-33474 not only makes the periphery of the cable larger in diameter on account of the thread-wound secured portion, but also causes the covering and the component under the covering to slip against each other due to loads on the cable that are imposed when the cable is bent, twisted, shifted, or otherwise disturbed, tending to displace the thread-wound secured portion out of its initial position upon shipment from the factory, possibly lowering the function to secure the cable.

BRIEF SUMMARY OF EMBODIMENTS

It is an object of the present disclosure to provide an endoscopic apparatus in which in the vicinity of a joint portion of a cable that is connected to an electronic circuit part of an endoscope, the cable is prevented from increasing in diameter by a securing member by which a component of the cable and a covering that covers the component are secured to each other, and the function to secure the component and the covering is prevented from being lowered by displacement of the securing member.

According to an aspect of the present disclosure, there is provided an endoscopic apparatus including a cable connected to an electronic circuit part of an endoscope, and a thread-like securing member that binds a covering of the cable, as a securing member that binds and secures the cable, in the vicinity of a joint portion of the cable that is connected to the electronic circuit part, in which the covering of the cable has an opening which is a recess formed by partly cutting out an outer circumferential area thereof on which the thread-like securing member binds and secures the covering, and the thread-like securing member has a portion that sinks in the opening and binds and secures the covering and a component of the cable that is exposed through the opening to each other.

According to another aspect of the present disclosure, there is provided an endoscopic apparatus including a cable connected to an electronic circuit part of an endoscope, and an engaging member, as a securing member that binds the cable, engaging a covering of the cable in the vicinity of a joint portion of the cable that is connected to the electronic circuit part, in which the covering of the cable has an opening which is a recess formed by partly cutting out an outer circumferential area thereof, and the engaging member has a portion that sinks in the opening and engages the covering and a component of the cable that is exposed through the opening.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

FIG. 2 is a view illustrating a configuration of a distal-end portion of an endoscope according to the first embodiment of the present disclosure.

DETAILED DESCRIPTION OF THE EMBODIMENTS

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

Embodiments of the present disclosure will hereinafter be described with reference to the drawings.

First Embodiment

Figure 1:
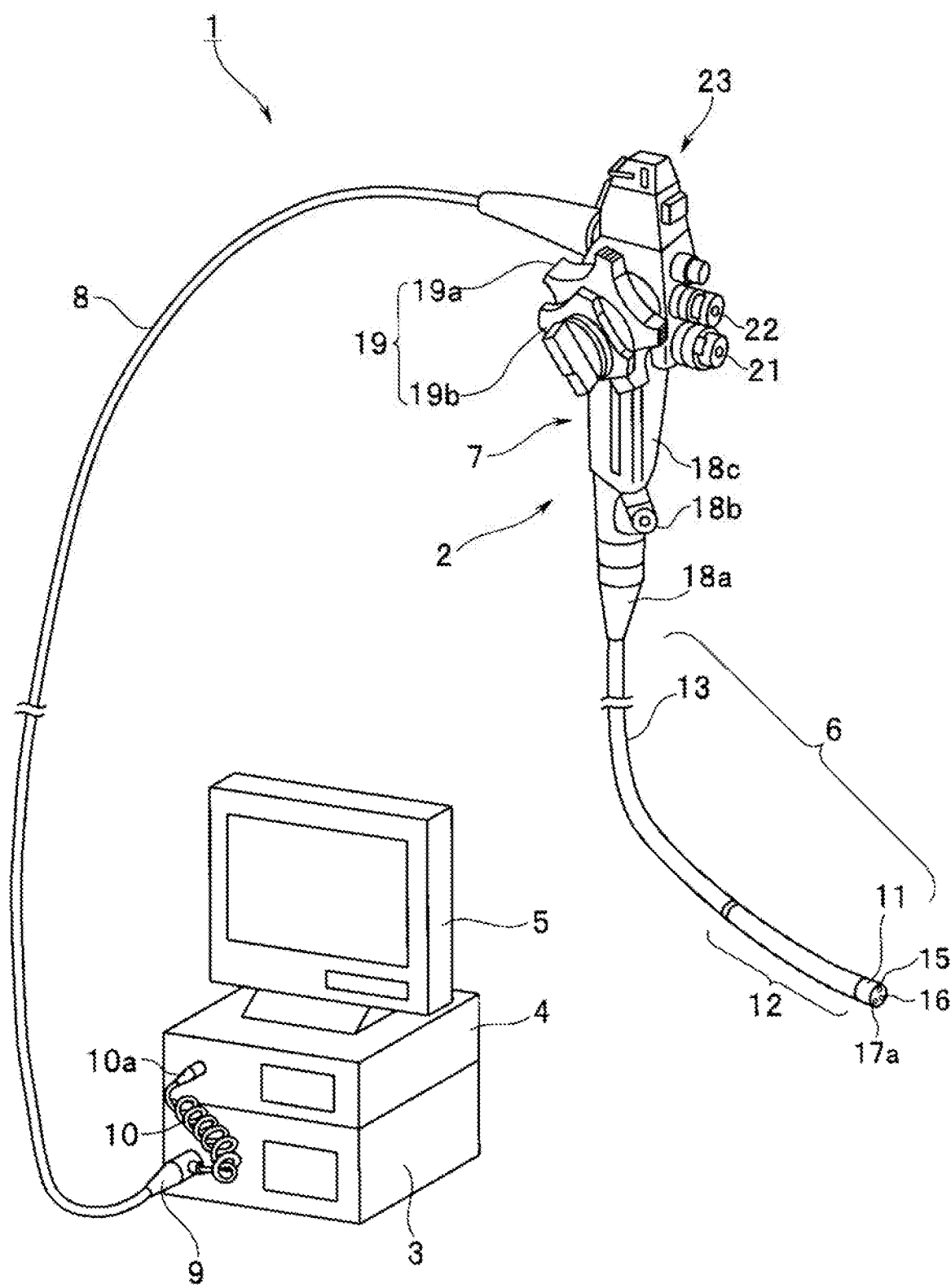
FIG. 1 is a view of an overall configuration of an endoscopic apparatus according to a first embodiment of the present disclosure.

FIG. 1 illustrates an endoscopic apparatus 1 that is constructed around an endoscope 2 as its core element. According to the present embodiment, the endoscopic apparatus 1 includes the endoscope 2, a light source apparatus 3 for supplying illuminating light to the endoscope 2, a video processor 4 as a signal processor for processing signals from an image capturing unit incorporated in the endoscope 2, and a color monitor 5 as a display apparatus for displaying endoscopic images.

The endoscope 2 includes a slender insertion portion 6 to be inserted into an examinee, a manipulator 7 disposed on the proximal end of the insertion portion 6, a universal cord 8 extending from the manipulator 7, and an endoscope connector 9 disposed on an end portion of the universal cord 8. The endoscope connector 9 is detachably connected to the light source apparatus 3, so that illuminating light from the light source apparatus 3 will be supplied through the universal cord 8 to a light guide, not illustrated, in the endoscope 2. A joint cable 10 has an end connected to the endoscope connector 9. An electric connector 10a on the other end of the joint cable 10 is detachably connected to a video processor 4. The video processor 4 is connected to the color monitor 5 through a video cable, not illustrated.

The insertion portion 6 of the endoscope 2 includes a hard distal-end portion 11 disposed on the distal end thereof, a bendable portion 12 disposed on a rear end of the distal-end portion 11, and a flexible tube portion 13 extending from a rear end of the bendable portion 12 to a front end of the manipulator 7.

Figure 2:
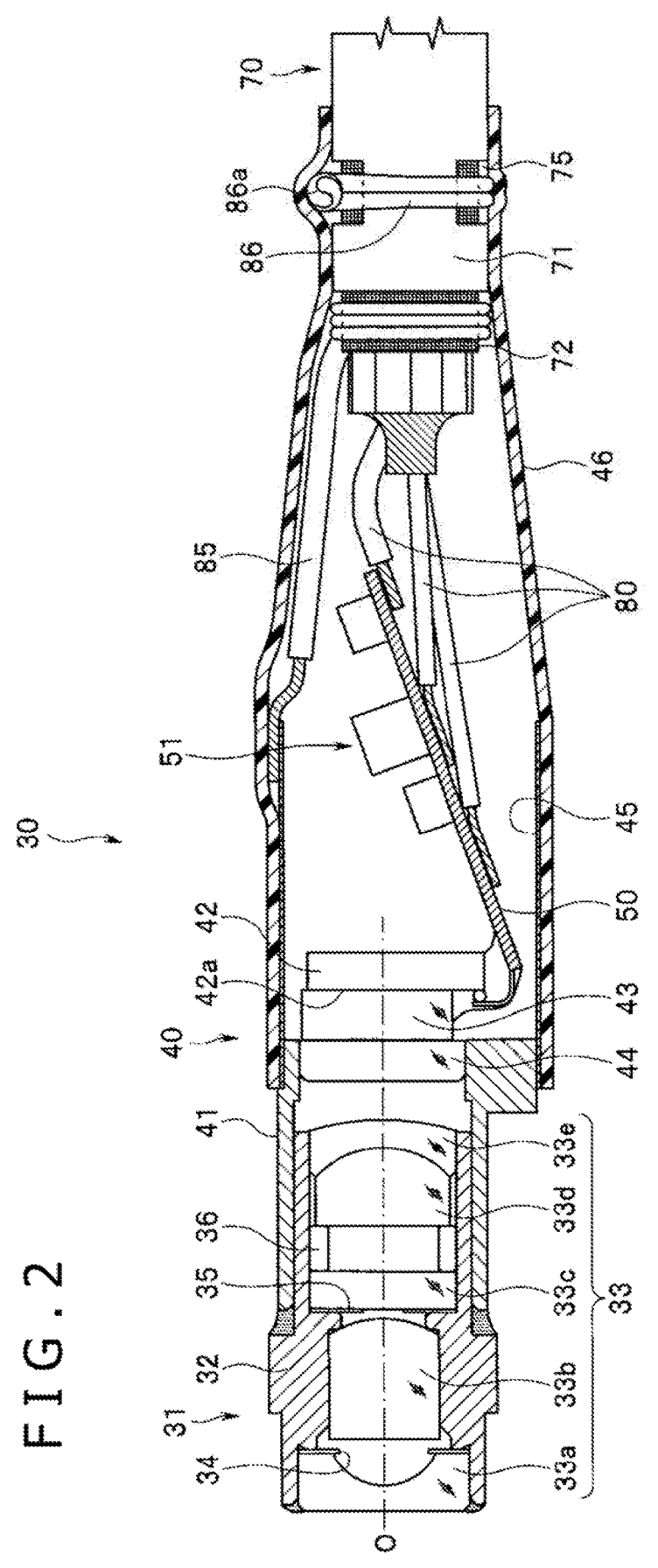

The distal-end portion 11 has on its distal-end face an observation window 15, a plurality of illumination windows 16, only one illustrated in FIG. 1, a distal-end opening 17a of a treatment tool channel, not illustrated, extending through the distal-end portion 11, and a cleaning nozzle, not illustrated. As illustrated in FIG. 2, an image capturing unit 30 housed in the distal-end portion 11 is disposed inwardly of the observation window 15, i.e., on a rear-face side of the observation window 15.

An illumination lens, not illustrated, is mounted in each of the illumination windows 16, and a light guide, not illustrated, for transmitting the illuminating light from the light source apparatus 3 is joined to the illumination lens. The illuminating light transmitted by the light guide is emitted through the illumination lens forwardly of the distal-end face of the distal-end portion 11, illuminating an observation target area in the examinee within the visual field of the image capturing unit 30.

The manipulator 7 includes a stiffener 18a for preventing the proximal end of the insertion portion 6 extending from the manipulator 7 from being bent, a treatment tool insertion port 18b disposed on a side of a lower portion of the manipulator 7, and a manipulator body 18c as a grip on an intermediate portion of the manipulator 7. The manipulator 7 also includes a bend manipulation assembly 19 including two bend manipulation knobs 19a, 19b on an upper portion of the manipulator 7, an air/water delivery controller 21, a suction controller 22, and a switch portion 23 including a plurality of switches primarily for controlling an image capturing function.

The treatment tool insertion port 18b of the manipulator 7 is held in fluid communication with the treatment tool channel in the insertion portion 6, which is open outwardly through the distal-end opening 17a in the distal-end portion 11.

Next, the image capturing unit 30 disposed in the distal-end portion 11 of the endoscope 2 will be described below with reference to FIG. 2.

The image capturing unit 30 is inserted and disposed in a distal-end hard member of the distal-end portion 11. The image capturing unit 30 is fastened sideways to the distal-end hard member by a screw or the like. The image capturing unit 30 has an observation optical system unit 31 making up an objective optical system that includes the observation window 15 and an image capturing device unit 40 joined to a rear-end side of the observation optical system unit 31.

According to the present embodiment, the observation optical system unit 31 has a lens frame 32 for holding lenses and a lens group 33 made up of a plurality of fixed lenses held by the lens frame 32. The lens frame 32 is of a substantially hollow cylindrical shape. The observation window 15 is made up of a first lens 33a disposed in the hollow cylindrical shape of the lens frame 32 on a distal-end side thereof. The lens group 33 includes a second lens 33b, a third lens 33c, a fourth lens 33d, and a fifth lens 33e that are disposed behind the first lens 33a and arranged successively along an optical axis O. These lenses are fixed to the lens frame 32 by an adhesive or the like.

Apertures 34 and 35 are disposed respectively behind the first lens 33a and the second lens 33b. The third lens 33c and the fourth lens 33d are spaced from each other by a spacer 36.

The observation optical system unit 31 described hereinbefore is coupled to the image capturing device unit 40. Incident light that enters through the lens group 33 is focused on a light detecting surface or image capturing surface of a solid-state image capturing chip 42, which includes a CCD, a CMOS, or the like, of the image capturing device unit 40. The solid-state image capturing chip 42 photoelectrically converts an optical image of a subject into a captured image signal, which is transmitted through the cable 70 to a signal processing circuit in a subsequent stage.

The image capturing device unit 40 has an image capturing device holding frame 41 that is of a substantially hollow cylindrical shape which holds the solid-state image capturing chip 42 therein. The lens frame 32 of the observation optical system unit 31 has a proximal-end side inserted and fitted in a distal-end side of the image capturing device holding frame 41. The lens frame 32 and the image capturing device holding frame 41 are hermetically joined to each other, thereby coupling the observation optical system unit 31 and the image capturing device unit 40 to each other.

A glass lid 43 for protecting the image capturing surface of the solid-state image capturing chip 42 is fixed to the image capturing surface 42a by an adhesive or the like. A positioning cover glass plate 44 is fixed to the glass lid 43 by an adhesive or the like. The cover glass plate 44 is fitted in a proximal-end side of the image capturing device holding frame 41 and fixed thereto by an adhesive or the like.

A circuit board 50 such as a flexible board, a rigid board, or the like is electrically connected to the solid-state image capturing chip 42. The circuit board 50 is a board on which there is mounted a video signal processing circuit made up of a plurality of electronic parts 51 including various integrated circuits, capacitors, resistors, transistors, and so on.

The circuit board 50 is disposed behind a rear surface of the solid-state image capturing chip 42, i.e., a reverse side of the image capturing surface 42a thereof. A plurality of leads 80 extending from the cable 70 are electrically connected to the circuit board 50 as an electronic circuit part. The cable 70 is inserted through the endoscope 2 and electrically connected to the video processor 4 through the electric connector 10a.

A hollow cylindrical reinforcing frame 45 is joined to the outer circumferential surface of a proximal end of the image capturing device holding frame 41. The reinforcing frame 45 has an outer circumferential surface on which there is disposed a heat-shrinkable tube 46 as a protective tube that covers up to a distal-end side of the cable 70. The proximal end of the image capturing device holding frame 41, the reinforcing frame 45, and the heat-shrinkable tube 46 jointly define a space therein which is filled up with a protective agent made of an insulative sealing resin or the like for holding and protecting the solid-state image capturing chip 42.

Figure 3:
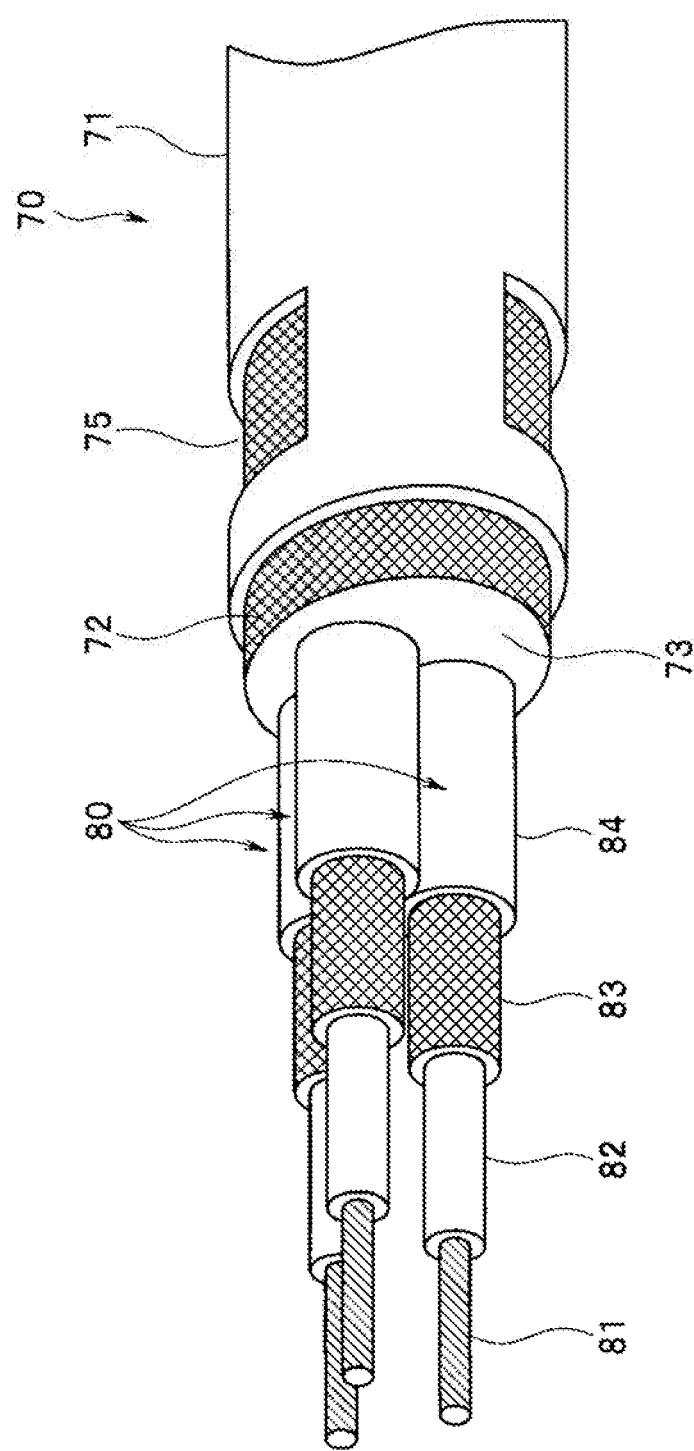
FIG. 3 is a view illustrating a configuration of a cable according to the first embodiment of the present disclosure.

According to the present embodiment, as illustrated in FIG. 3, the cable 70 includes a multi-core cable having a plurality of leads 80 disposed in a covering 71 as a cladding made of an insulative resin material or the like. Specifically, as a component in the covering 71, there is disposed a shield layer 72 made up of a plurality of twisted metal strands disposed under the covering 71. A sheath 73 made of a dielectric material or the like is covered with the shield layer 72, and holds the leads 80 therein.

Each of the leads 80 includes a coaxial wire including a conductive core wire 81 covered with an insulator 82, a shield layer 83 made of a plurality of twisted metal strands in the form of a net and covering the insulator 82, and an insulative sheath 84 covering the shield layer 83. In FIG. 3, the conductive core wire 81 is illustrated as being made up of a plurality of metal strands. However, the conductive core wire 81 may be made up of a single wire.

For connecting the cable 70 to the circuit board 50, a portion of the covering 71 is cut off on the distal-end side of the cable 70, exposing the shield layer 72. The plurality of leads 80 are extended from the sheath 73, and the conductive core wires 81 are exposed. An end portion of the covering 71 is tightened to prevent the covering 71 from being displaced from the end of the cable 70 due to loads on the cable 70 that are imposed when the cable 70 is bent, twisted, shifted, or otherwise disturbed.

Specifically, as illustrated in FIG. 2, an end portion of a jumper wire 85 is wound on the exposed position of the shield layer 72 on the end portion of the cable 70 and fixed thereto by soldering, electrically conductive adhesive bonding, or the like. The other end of the jumper wire 85 is attached to the reinforcing frame 45 as an electrically conductive frame by soldering, electrically conductive adhesive bonding, or the like. In other words, the shield layer 72 and the reinforcing frame 45 are electrically connected to each other by the jumper wire 85, keeping the shield layer 72 at the ground potential. The conductive core wires 81 of the leads 80 are connected by soldering to a predetermined land on the circuit board 50, thereby establishing an electric connection between the cable 70 and the circuit board 50.

The covering 71 of the cable 70 is bound by a binding thread 86 as a securing member for securing the cable 70 in the vicinity of a joint portion of the cable 70 that is connected to the circuit board 50. The binding thread 86 includes a thread-like securing member such as a metal wire, a nylon string, or the like. The covering 71 is secured in position by the binding thread 86 as a securing member at a plurality of slit-like openings 75 defined in the covering 71 at a predetermined position axially spaced from the end of the covering 71.

Figure 4:
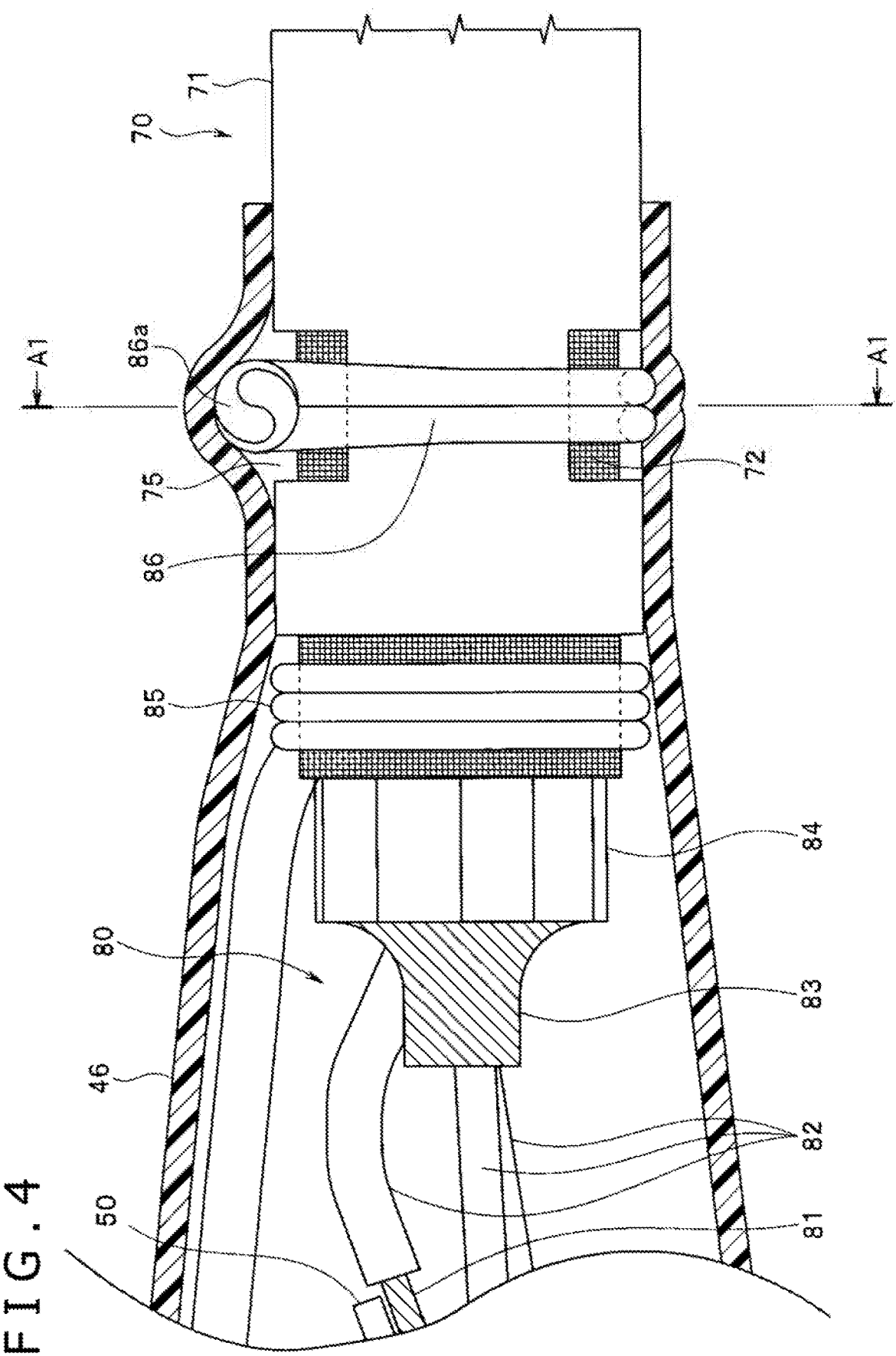
FIG. 4 is an enlarged view illustrating a securing structure at an end portion of the cable that is connected to a circuit board according to the first embodiment of the present disclosure.
Figure 5:
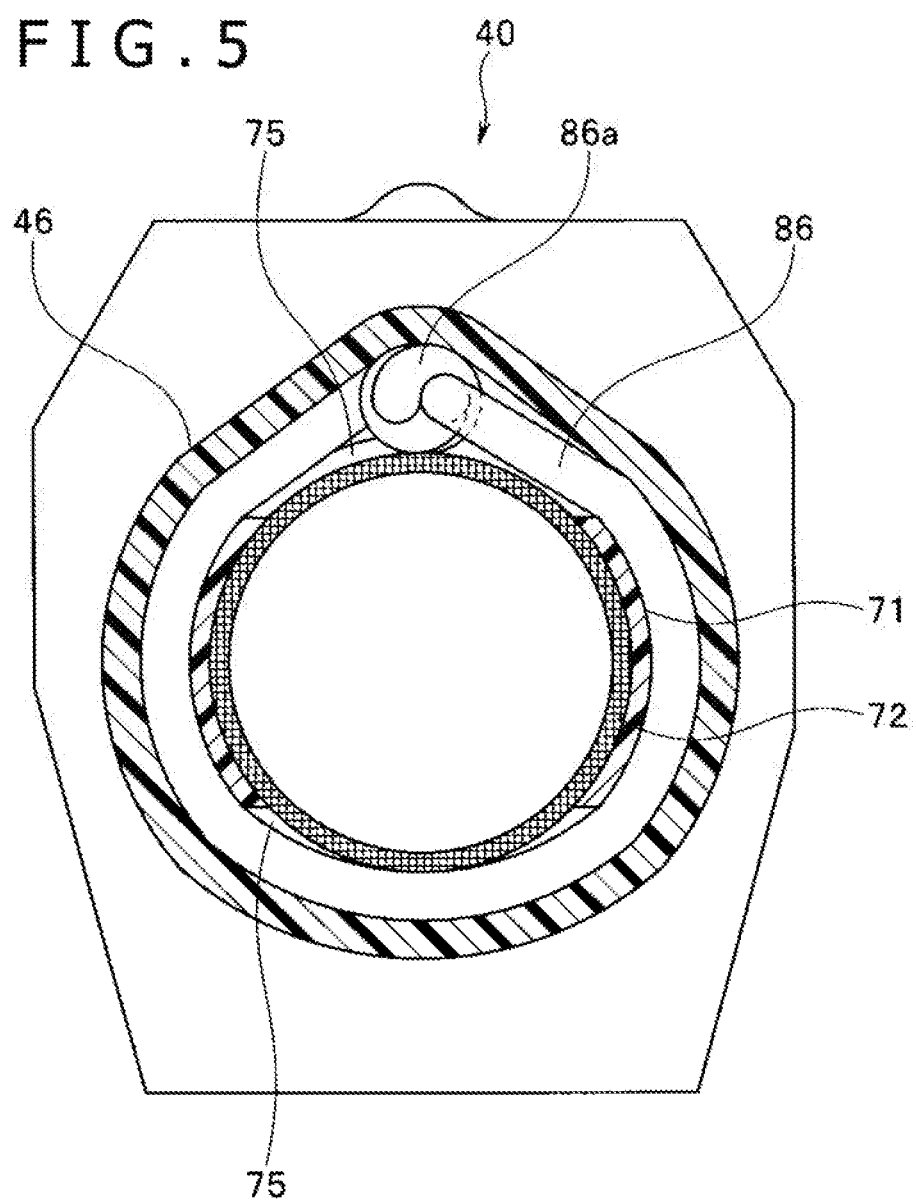
FIG. 5 is a cross-sectional view taken along line A1-A1 of FIG. 4 according to the first embodiment of the present disclosure.

The openings 75 are in the shape of slit-like recesses axially spaced a certain distance from the end of the covering 71 and circumferentially spaced around the covering 71 at a plurality of angularly spaced locations on the outer circumference of the covering 71. The shield layer 72 is exposed through the slit-like opening 75. According to the present embodiment, as illustrated in FIGS. 4 and 5, the openings 75 are spaced at equal intervals circumferentially around the covering 71. Specifically, the openings 75 are defined at two positions that are diametrically opposite each other.

The binding thread 86 is wound into a plurality of turns around the covering 71 across the openings 75. At least one of the turns of the binding thread 86 extends over the covering 71 and sinks from an outer surface of the covering 71 onto the shield layer 72 under the covering 71. The covering 71 is bound by the binding thread 86 that is tied into a knot as a securing portion 86a positioned on the shield layer 72 in one of the openings 75. Thereafter, the covering 71 is covered with the heat-shrinkable tube 46 so as to cover at least the binding thread 86, securing the covering 71 and the sheath 73 and the leads 80 that are covered with the shield layer 72 reliably in place.

According to the present embodiment, as described hereinbefore, when the cable 70 is connected to the circuit board 50, the end of the cable 70 is secured in place by a securing structure in which the binding thread 86 sinks into one of the openings 75 defined partly in the outer circumference of the covering 71 of the cable 70. Compared with the conventional structure in which the binding thread 86 is tied into a knot placed in its entirety on the outer surface of the covering 71, the distance that the securing portion 86a projects radially outwardly is smaller, making the periphery of the cable 70 smaller in diameter. In addition, the securing portion 86a is less liable to be displaced on the covering 86a, preventing the function to bind the covering 71 from being lowered.

Furthermore, the end of the covering 71 and the securing portion 86a are rendered positionally stable relatively to each other without wobbling, making it possible to shorten the length of the cable 70 from the end thereof to the securing portion 86, which is hardened when connected to the circuit board 50, without impairing stability thereof.

The binding thread 86 may be an electrically conductive thread such as a metal wire or the like. The binding thread 86 that is electrically conductive may be electrically connected to the jumper wire 85 or may alternatively be extended into a length for use as a jumper wire equivalent in place of the jumper wire 85.

Specifically, in FIGS. 4 and 5, the securing portion 86a is formed as a knot of the binding thread 86. However, as illustrated in FIGS. 6 and 7, the binding thread 86 may be fixed to the shield layer 72 as a metal member exposed through the openings 75 by soldering, electrically conductive adhesive bonding, or the like, forming a securing portion 86b.

In the securing portion 86b, the shield layer 72 and the binding thread 86 are electrically connected to each other, and the jumper wire 85 is connected to the binding thread 86. Alternatively, the binding thread 86 that is electrically connected to the shield layer 72 in one of the openings 75 may be extended into a length having a distal end electrically connected to the reinforcing frame 45, so that the extended length of the binding thread 86 may be used as a jumper wire equivalent in place of the jumper wire 85.

In this manner, the distance that the securing portion 86b projects radially outwardly is made smaller. Moreover, the shield layer 72 for connection to the jumper wire 85 does not need to be exposed from the end of the covering 71, so that the length of the hardened end portion of the cable 70 can be reduced.

Figure 6:
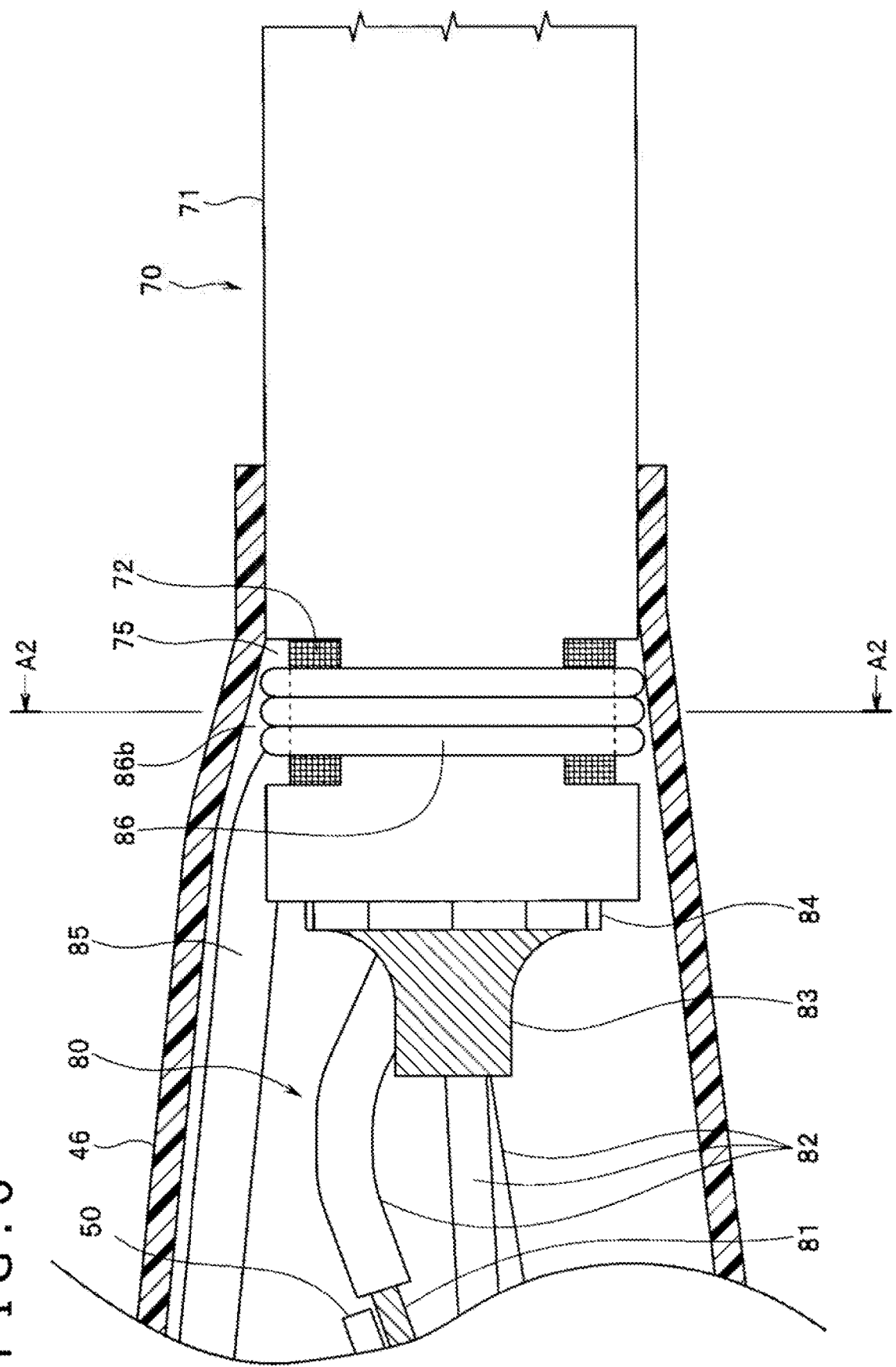
FIG. 6 is a view illustrating another securing structure at the end portion of the cable according to the first embodiment of the present disclosure.
Figure 7:
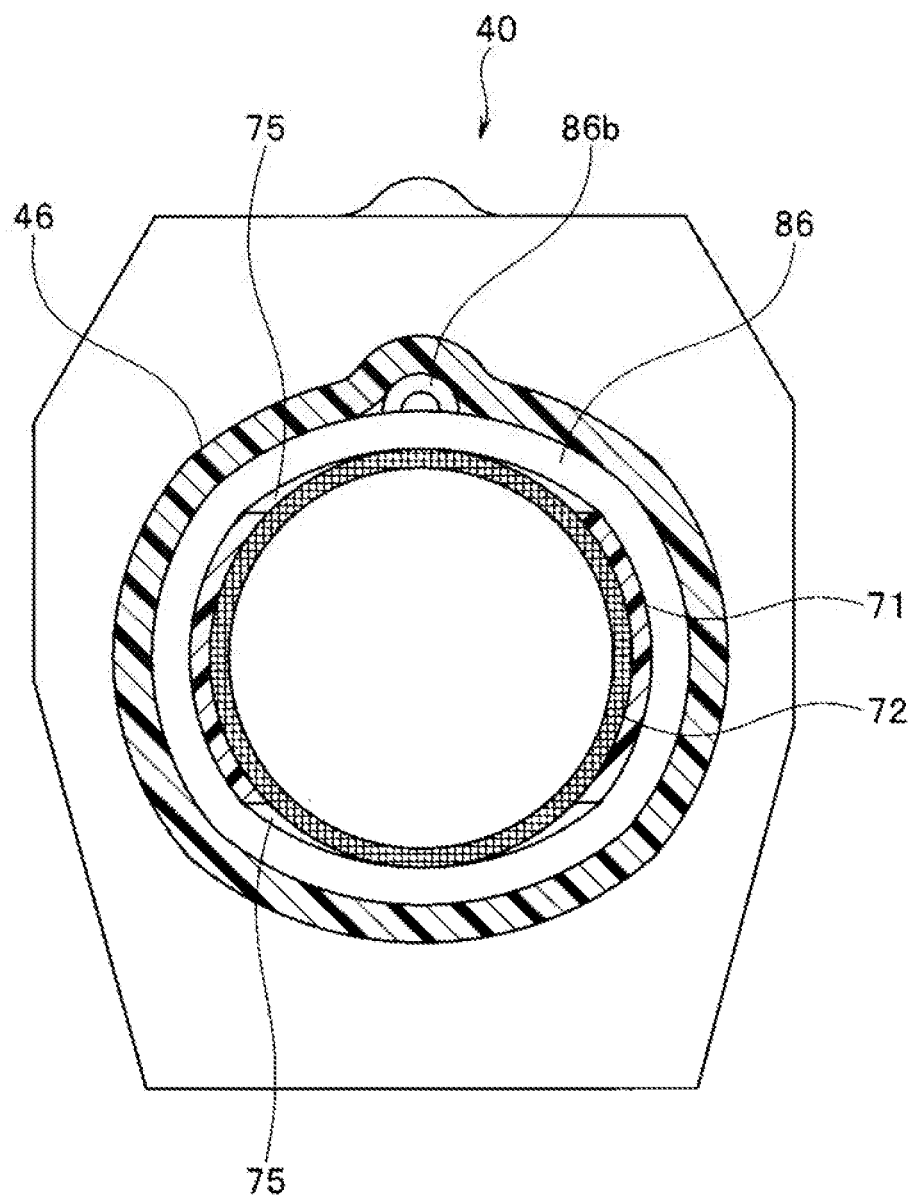
FIG. 7 is a cross-sectional view taken along line A2-A2 of FIG. 6 according to the first embodiment of the present disclosure.

The securing structure illustrated in FIGS. 6 and 7 is applicable where the binding thread 86 is electrically non-conductive. In such an application, the jumper wire 85 is electrically connected to the shield layer 72 through one of the openings 75.

Various processes on the end of the cable 70, such as the cutting-off of an end portion of the covering 71, the formation of the openings 75, and the processing on the shield layer 72, etc. may be carried out by a laser apparatus. For example, the covering 71 of the cable 70 may be melted away at a position over the shield layer 72 by a laser beam applied thereto. The openings 75 may be formed by removing certain shaped portions of the covering 71 over the shield layer 72 with a laser beam applied thereto. Using a laser beam to cut off an end portion of the covering 71 and form the openings 75 in the covering 71 is effective to increase the dimensional stability of the covering 71.

If a metal wire is used as the binding thread 86, then the binding thread 86 may be fused by a laser beam applied thereto, producing a securing portion 86a or 86b shaped as a smaller knot. With this arrangement, not only the distance that the securing portion 86a or 86b projects radially outwardly is made smaller, but also the length of the hardened end portion of the cable 70 is prevented from varying due to seeped-in solder compared with the binding thread 86 soldered to the shield layer 72.

Figure 8:
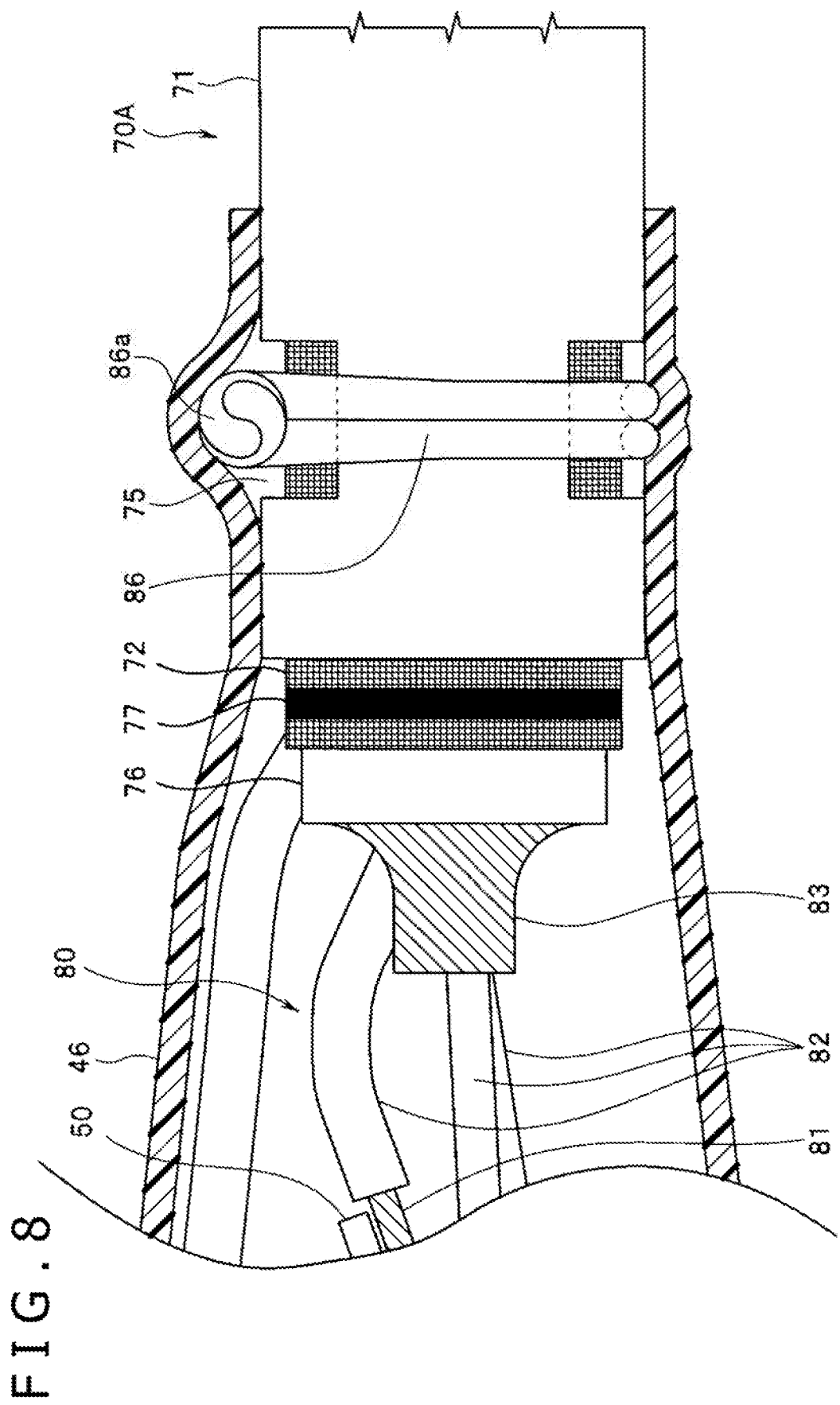
FIG. 8 is a view illustrating still another securing structure at the end portion of the cable according to the first embodiment of the present disclosure.

Furthermore, as illustrated in FIG. 8, a cable 70A, which is a slight structural modification of the cable 70, may include a metal-evaporated film 76 disposed as a layer directly under the shield layer 72. The shield layer 72 may then be cut and fused by a laser apparatus. The metal-evaporated film 76 may made of a composite material of aluminum foil and polyester film that are bonded together.

With the metal-evaporated film 76 disposed as a layer under the shield layer 72, the end portion of the shield layer 72 can be cut by a laser beam applied thereto. In the vicinity of the cut edge, the shield layer 72 may be densely welded fully circumferentially to form an annular welded strip 77. The welded strip 77 serves the function of a metal O-ring for blocking the entry of humidity into the cable 70A while the endoscope 2 is being sterilized in an autoclave. Part of the welded strip 77 may be formed in the openings 75 or the binding thread 86 and the shield layer 72 may be densely welded to form part of the welded strip 77 in the openings 75 thereby to prevent the covering 71 from being displaced more reliably.

In the present embodiment, the multi-core cable as illustrated in FIG. 3 has been illustrated as the cable 70 connected to the circuit board 50. Other cables connected to electronic circuit parts other than the circuit board 50, e.g., cables according to structural examples 1 through 4 illustrated in FIGS. 9 through 12, may incorporate any of the same securing structures as those described hereinbefore.

Figure 9:
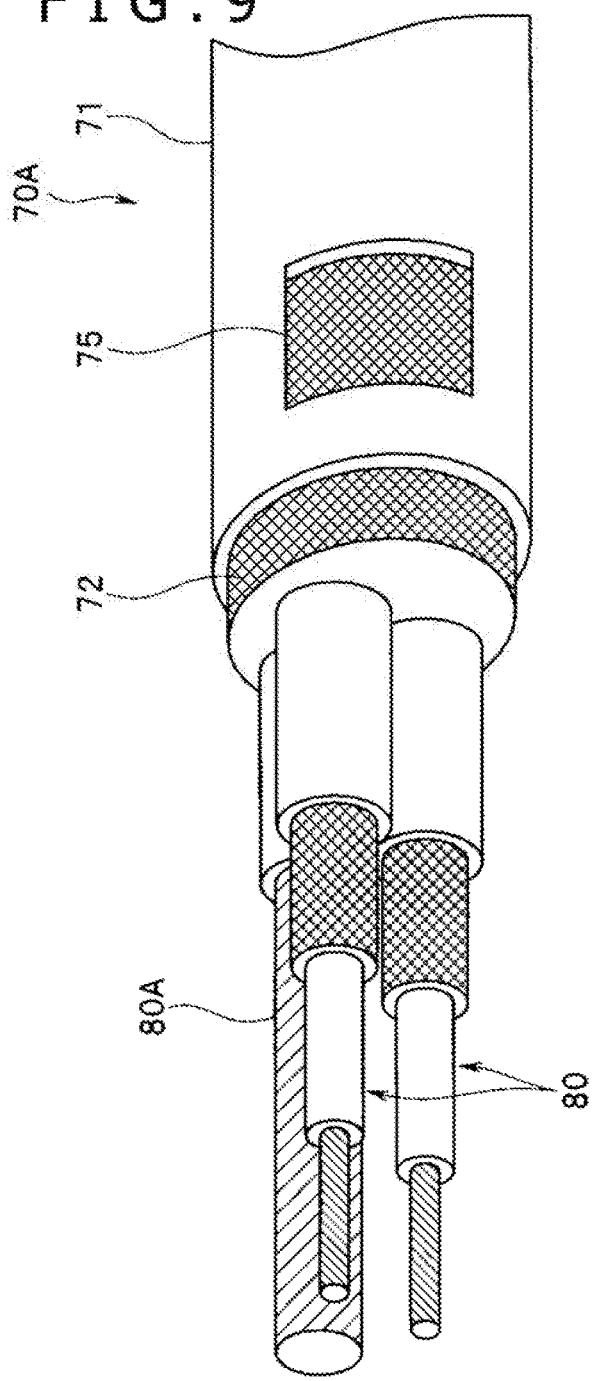
FIG. 9 is a view illustrating other configuration example 1 of cable.

A cable 70A according to the structural example 1 illustrated in FIG. 9 includes a composite cable in which one of the leads 80 of the cable 70 is replaced with a simple wire 80A. In the cable 70A, the binding thread 86 sinks into one of the slit-like openings 75 defined partly in the outer circumference of the covering 71 and is tied into a knot. The knot of the binding thread 86 is effective to prevent the covering 71 from being displaced from the end of the cable 70 due to loads on the cable 70 that are imposed when the cable 70 is bent, twisted, shifted, or otherwise disturbed.

Figure 10:
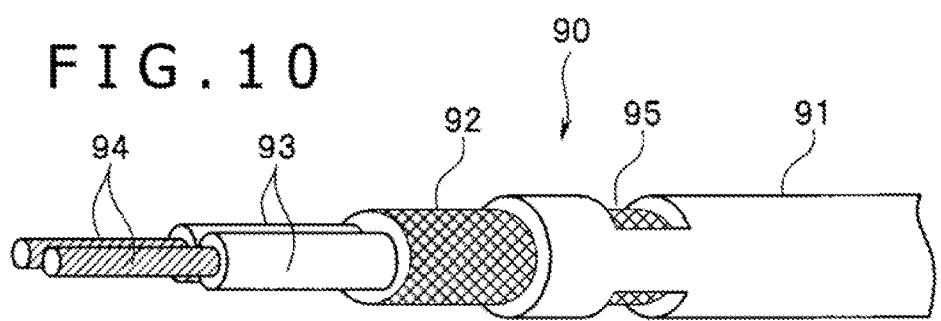
FIG. 10 is a view illustrating other configuration example 2 of cable.

A cable 90 according to the structural example 2 illustrated in FIG. 10 has a shield layer 92 under a covering 91, as is the case with the cable 70. The cable 90 includes two conductive core wires 94 covered with respective insulators 93 within the shield layer 92. The cable 90 similarly has slit-like openings 95 defined partly in the outer circumference of the covering 91. The binding thread 86 that sinks into the openings 95 and are tied into a knot is effective to prevent the covering 91 from being displaced from the end of the cable 90.

Figure 11:
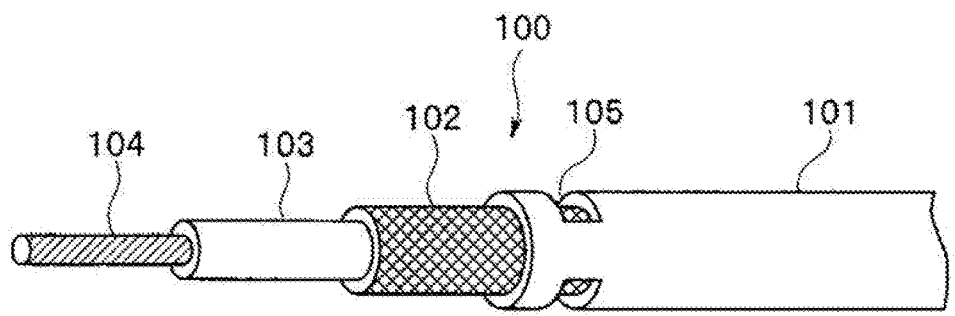
FIG. 11 is a view illustrating other configuration example 3 of cable.

A cable 100 according to the structural example 3 illustrated in FIG. 11 includes a single-core coaxial cable. The cable 100 has a shield layer 102 under a covering 101 and a conductive core wire 104 disposed in the shield layer 102 and covered with an insulator 103, as is the case with the cable 70. The cable 100 similarly has slit-like openings 105 defined partly in the outer circumference of the covering 101. The binding thread 86 that sinks into the openings 95 and are tied into a knot is effective to prevent the covering 101 from being displaced from the end of the cable 90.

Figure 12:
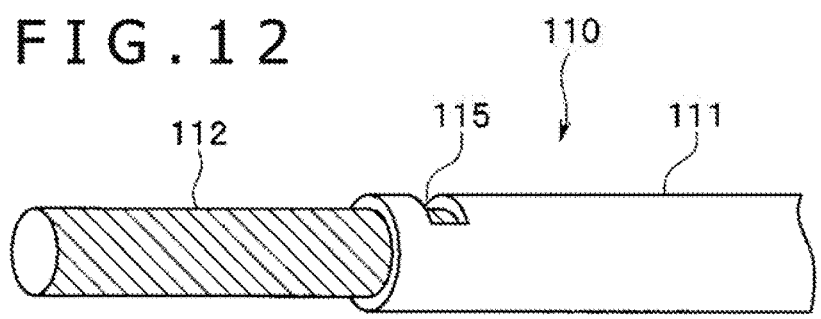
FIG. 12 is a view illustrating other configuration example 4 of cable.

Furthermore, a cable 110 according to the structural example 4 illustrated in FIG. 12 includes a single-core coaxial cable. The cable 110 has a conductive core wire 112 and covered with a covering 111. The cable 110 similarly has slit-like openings 115 defined partly in the outer circumference of the covering 111. The binding thread 86 that sinks into the openings 115 and are tied into a knot is effective to prevent the covering 111 from being displaced from the end of the cable 110.

Second Embodiment

Next, a second embodiment will be described below. According to the second embodiment, there is illustrated a securing structure for a cable end in the switch portion 23 disposed on the manipulator 7 of the endoscope 2.

Figure 13:
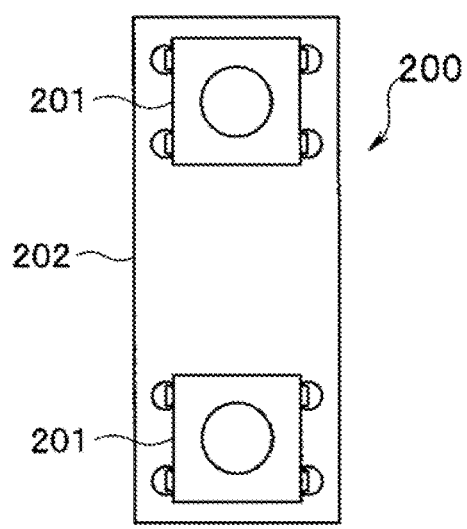
FIG. 13 is a front elevational view of a switch unit according to a second embodiment of the present disclosure.

As illustrated in FIG. 13, for example, a switch unit 200 in which two switches 201 are mounted on a board 202 is incorporated in the switch portion 23. In such an arrangement, the end of a cable that is connected to the switch unit 200 is secured by the same securing structure as the securing structure according to the first embodiment.

Figure 14:
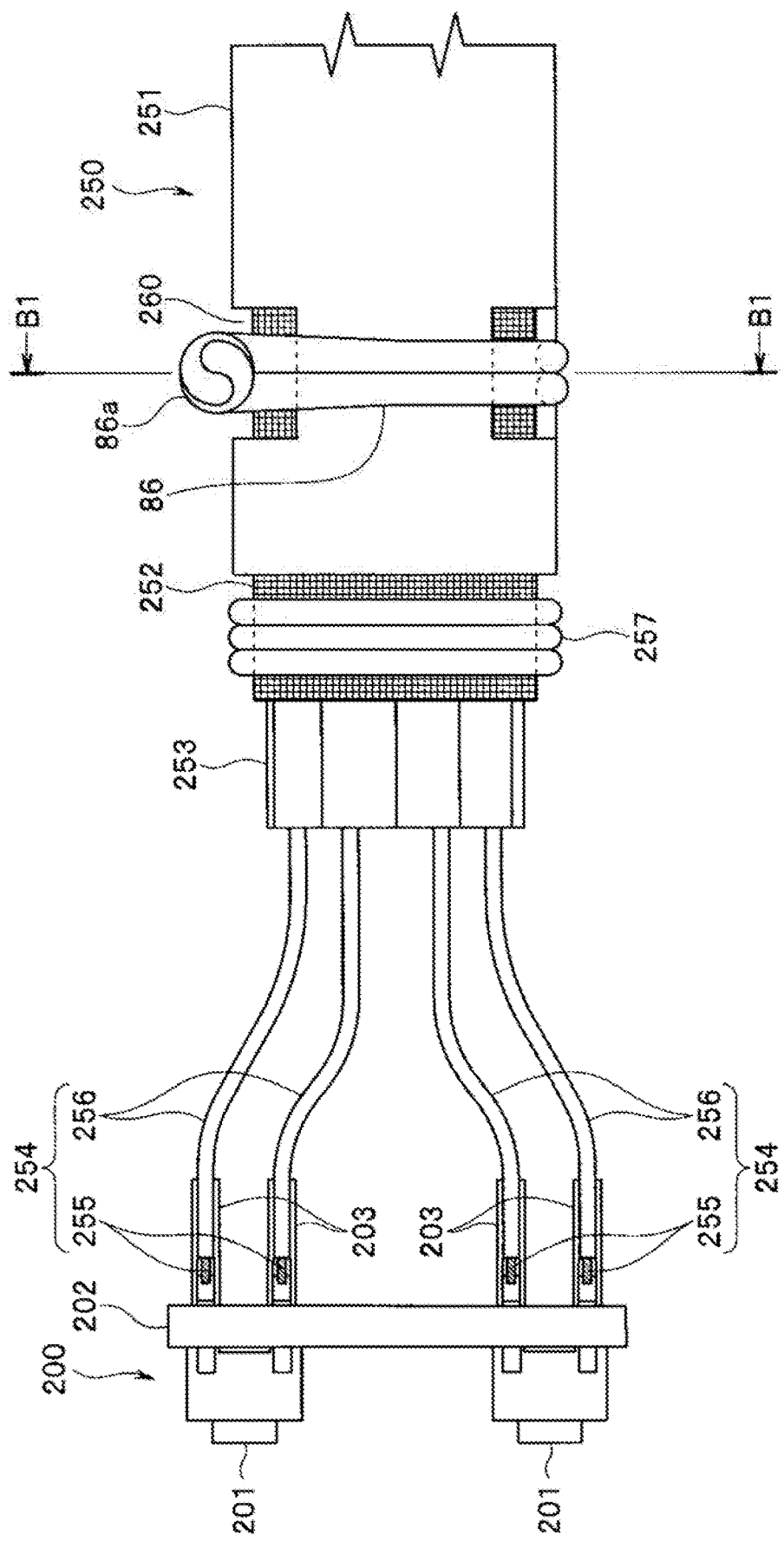
FIG. 14 is a view illustrating a securing structure at an end portion of a cable that is connected to the switch unit according to the second embodiment of the present disclosure.
Figure 15:
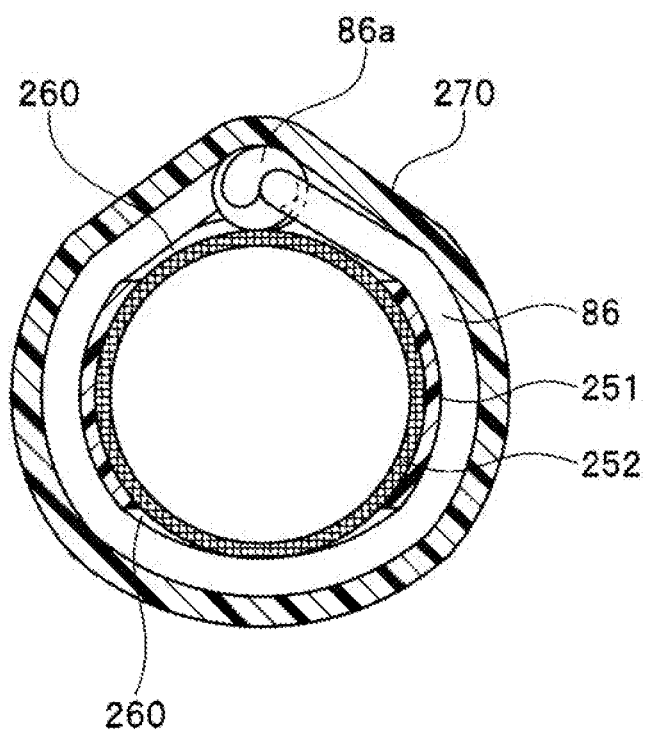
FIG. 15 is a cross-sectional view taken along line B1-B1 of FIG. 14 according to the second embodiment of the present disclosure.

As illustrated in FIGS. 14 and 15, a cable 250 connected to the switch unit 200 includes a multi-core cable similar to the cable 70 according to the first embodiment. Specifically, the cable 250 has a shield layer 252 under a covering 251 and a sheath 253 under the shield layer 252. The sheath 253 holds a plurality of leads 254 each including a conductive core wire 255 covered with an insulator 256.

The leads 254 that extend from the cable 250 have portions of the conductive core wires 255 exposed from their distal ends. The exposed portions of the conductive core wires 255 are fixed to respective terminals 203 projecting from a rear surface of the board 202 that supports the switches 201, by soldering, electrically conductive adhesive bonding, or the like. The switches 201 are thus electrically connected to the leads 254. According to the present embodiment, each of the switches 201 includes a two-pole switch, and two of the leads 254 are connected to each switch 201.

The covering 251 of the cable 250 has a plurality of slit-like openings 260, each of a predetermined width, defined therein at a predetermined position axially spaced from the end of the covering 251 and circumferentially spaced around the covering 251 at a plurality of angularly spaced locations on the outer circumference of the covering 251. The shield layer 252 is exposed through the slit-like opening 260. In FIGS. 14 and 15, the openings 260 are defined at two positions that are diametrically opposite each other on the outer circumference of the covering 251.

The covering 251 of the cable 250 is bound by a binding thread 86 in the same manner as with the first embodiment. The binding thread 86 is wound into a plurality of turns around the covering 251 across the openings 260. At least one of the turns of the binding thread 86 extends over the covering 251 and sinks from an outer surface of the covering 251 onto the shield layer 252 under the covering 251. The covering 251 is bound by the binding thread 86 that is tied into a knot as a securing portion 86a positioned on the shield layer 252 in one of the openings 260. Thereafter, the covering 251 and the binding thread 86 are covered with a heat-shrinkable tube 270, securing the leads 254 reliably in place within the covering 251 and the shield layer 252.

Figure 16:
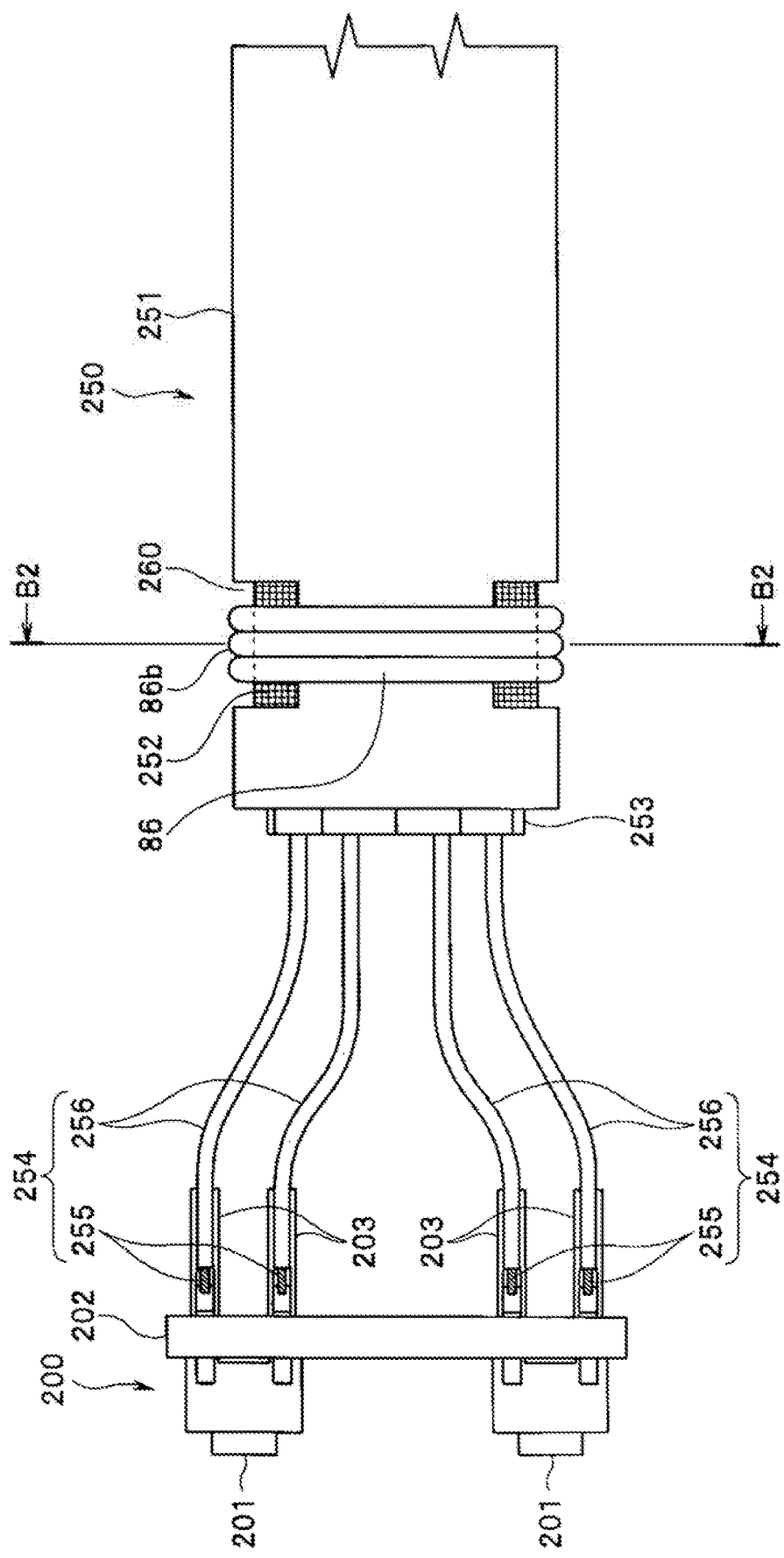
FIG. 16 is a view illustrating another securing structure at the end portion of the cable that is connected to the switch unit according to the second embodiment of the present disclosure.

In FIG. 14 and FIG. 16 to be referred to hereinafter, the heat-shrinkable tube 270 is omitted from illustration. In FIG. 14, a conductive core wire 257 wound around the portion of the shield layer 252 that is exposed on the terminal end of the cable 250 functions as a ground conductor.

Figure 17:
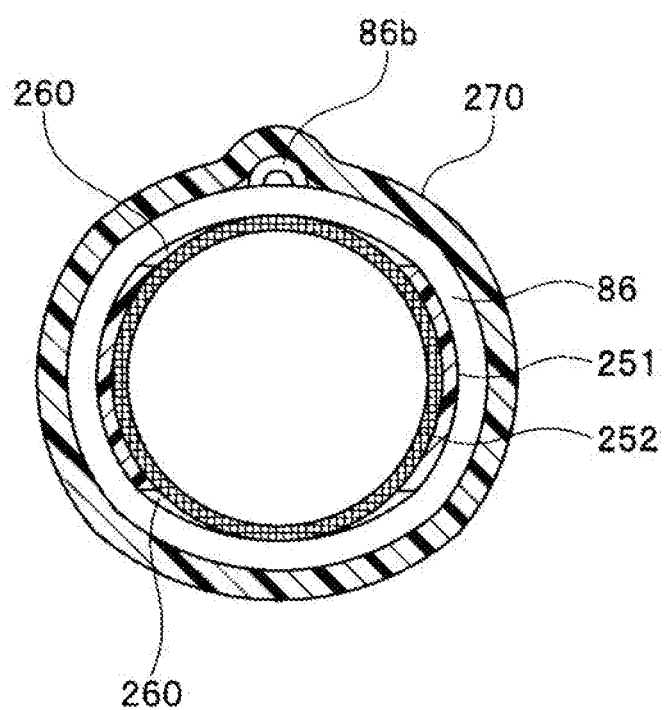
FIG. 17 is a cross-sectional view taken along line B2-B2 of FIG. 16 according to the second embodiment of the present disclosure.

The cable 250 may incorporate a securing structure illustrated in FIGS. 16 and 17. Specifically, the binding thread 86 is fixed to the portions of the shield layer 252 that are exposed through the openings 260 and secured thereto by soldering, electrically conductive adhesive bonding, fusion based on a laser beam applied thereto, or the like, thereby providing securing portions 86b. Therefore, the distance that the securing portions 86b project radially outwardly is made smaller, and the length of the hardened end portion of the cable 250 can be reduced.

According to the second embodiment, as is the case with the first embodiment, the covering is prevented from being displaced from the end of the cable due to loads on the cable that are imposed when the cable is bent, twisted, shifted, or otherwise disturbed. Furthermore, the distance that the securing portions 86a and 86b which secure the binding thread 86 project radially outwardly is reduced, preventing the cable from increasing in diameter. Moreover, the end of the covering and the securing portions are made positionally constant, making it possible to shorten the hardened length of the cable without impairing stability thereof.

Third Embodiment

Next, a third embodiment of the present disclosure will be described below. According to the third embodiment, there is illustrated a securing structure for a cable end in the electric connector by which the endoscope 2 is connected to the video processor 4.

Figure 18:
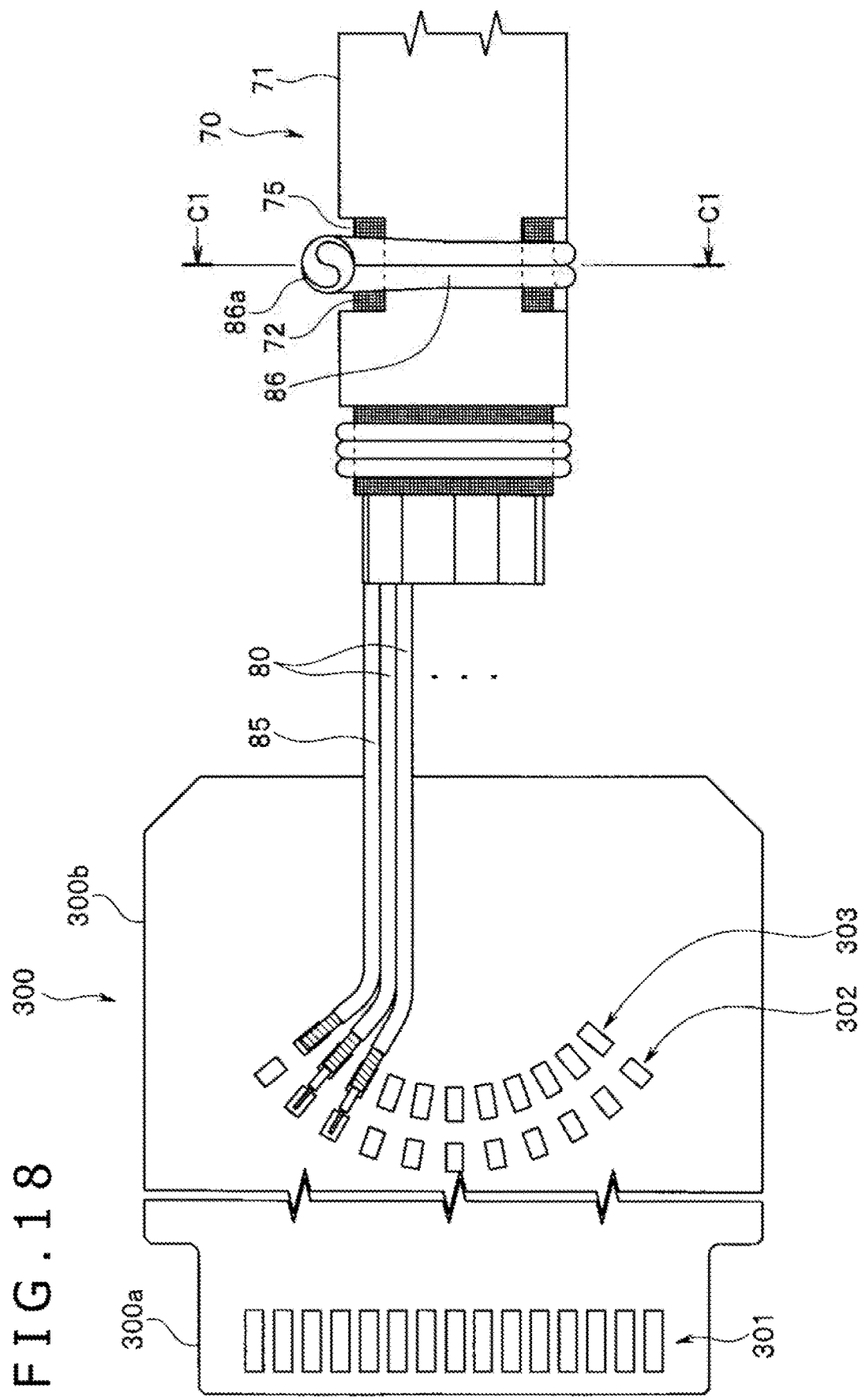
FIG. 18 is a view illustrating a securing structure at an end portion of a cable that is connected to an electric connector according to a third embodiment of the present disclosure.

FIG. 18 illustrates an example in which the electric connector 10a according to the first embodiment includes a flat connector, for example. The flat connector has a connector board 300 to which a cable is connected. The cable connected to the connector board 300 is of the same structure as the cable 70 that is connected to the circuit board 50 of the image capturing unit 30 according to the first embodiment. Parts of the cable are denoted by identical reference characters to those of the cable 70 and will not be described in detail hereinafter.

The connector board 300 has an edge connector portion 300a with an array of contacts 301 disposed thereon and a terminal portion 300b having a plurality of lands 302 that are individually electrically connected to the respective contacts 301 on the edge connector portion 300a through a predetermined printed pattern, not illustrated. The lands 302 are paired with respective ground lands 303 on the terminal portion 300b.

The connector board 300 and the cable 70 are connected to each other by the leads 80 extending from the cable 70. The leads 80 are fixed to the lands 302 connected to the respective contacts 301 by soldering, electrically conductive adhesive bonding, or the like, so that the contacts 301 and the leads 80 are electrically connected to each other. Jumper wires 85 have end portions wound around the portion of the shield layer 72 that is exposed on the terminal end of the cable 70 and fixed thereto by soldering, electrically conductive adhesive bonding, or the like. The other ends of the jumper wires 85 are soldered to the ground lands 303.

Figure 19:
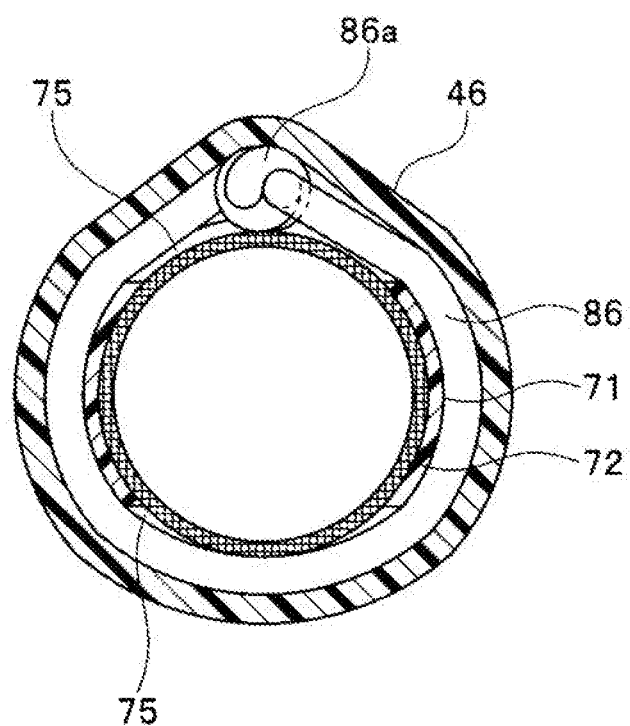
FIG. 19 is a cross-sectional view taken along line C1-C1 of FIG. 18 according to the third embodiment of the present disclosure.

The covering 71 of the cable 70 is secured in place by being bound by the binding thread 86. The binding thread 86 is wound into a plurality of turns around the covering 71 across the openings 75. At least one of the turns of the binding thread 86 extends over the covering 71 and sinks from an outer surface of the covering 71 onto the shield layer 72 under the covering 71. The covering 71 is bound by the binding thread 86 that is tied into a knot as a securing portion 86a positioned on the shield layer 72 in one of the openings 75. Thereafter, the covering 71 and the binding thread 86 are covered with the heat-shrinkable tube 46 (see FIG. 19), securing the leads 80 reliably in place within the covering 71 and the shield layer 72.

Figure 20:
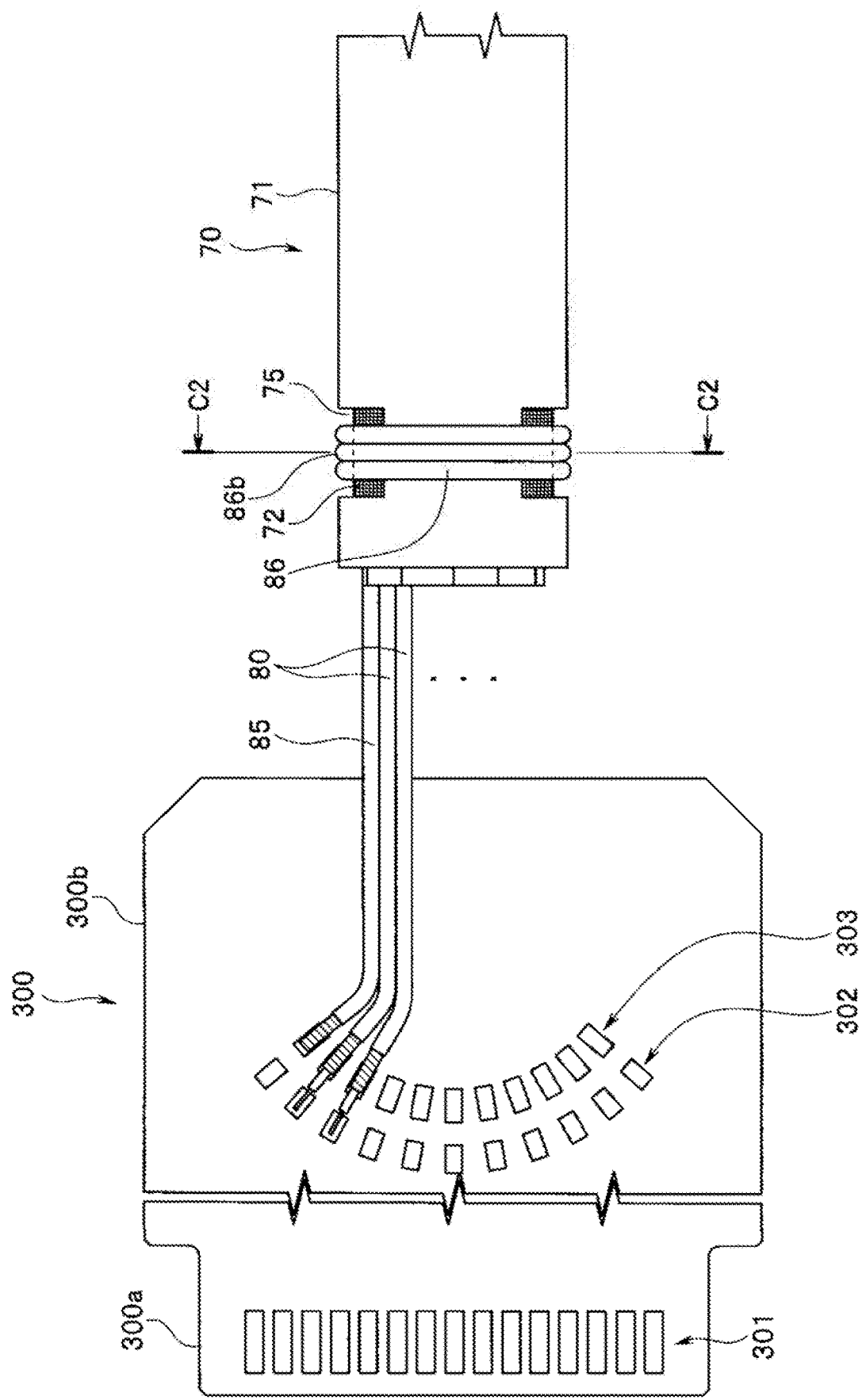
FIG. 20 is a view illustrating another securing structure at the end portion of the cable that is connected to the electric connector according to the third embodiment of the present disclosure.
Figure 21:
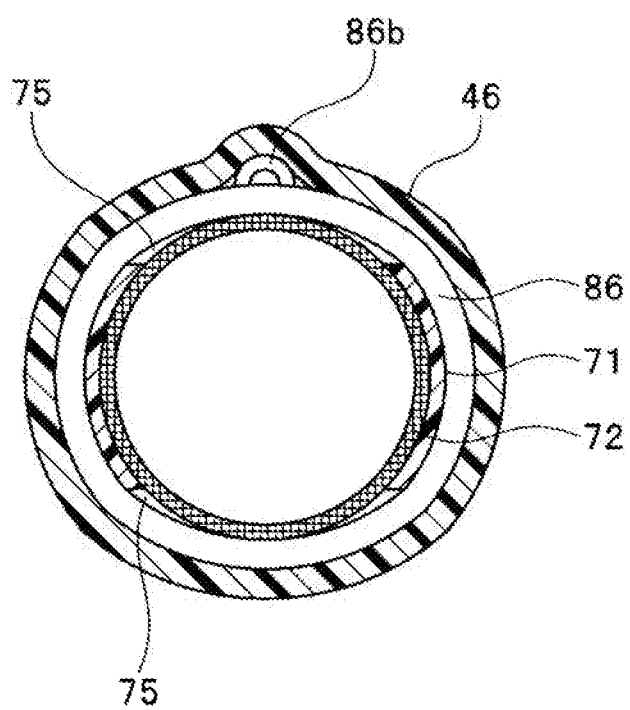
FIG. 21 is a cross-sectional view taken along line C2-C2 of FIG. 20 according to the third embodiment of the present disclosure.

Alternatively, as illustrated in FIGS. 20 and 21, the binding thread 86 may be fixed to the portions of the shield layer 72 that are exposed through the openings 75 and secured thereto by soldering, electrically conductive adhesive bonding, or the like, thereby providing securing portions 86b. A securing structure may be provided by electrically connecting the shield layer 72 and the binding thread 86 and the jumper wires 85 are connected to the binding thread 86. In such an arrangement, the binding thread 86 electrically connected to the shield layer 72 may be extended through the openings 75 and may have its distal end electrically connected to the lands 303.

The securing structure illustrated in FIGS. 20 and 21 makes it possible to further reduce the distance that the securing portions 86b project radially outwardly. Moreover, the shield layer 72 for connection to the jumper wires 85 does not need to be exposed from the end of the covering 71, so that the length of the hardened end portion of the cable 70 can further be reduced.

Figure 22:
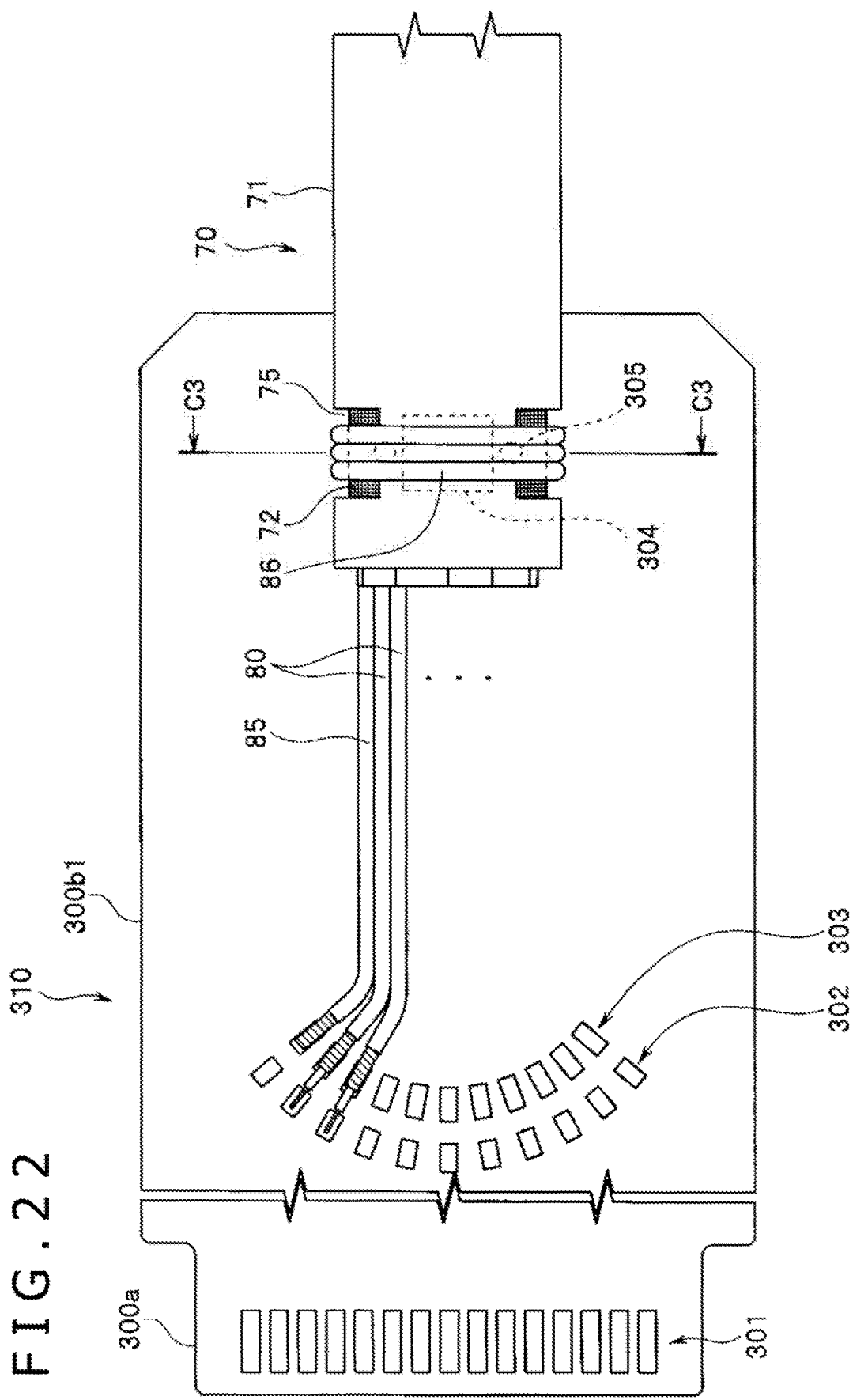
FIG. 22 is a view illustrating still another securing structure at the end portion of the cable that is connected to the electric connector according to the third embodiment of the present disclosure.
Figure 23:
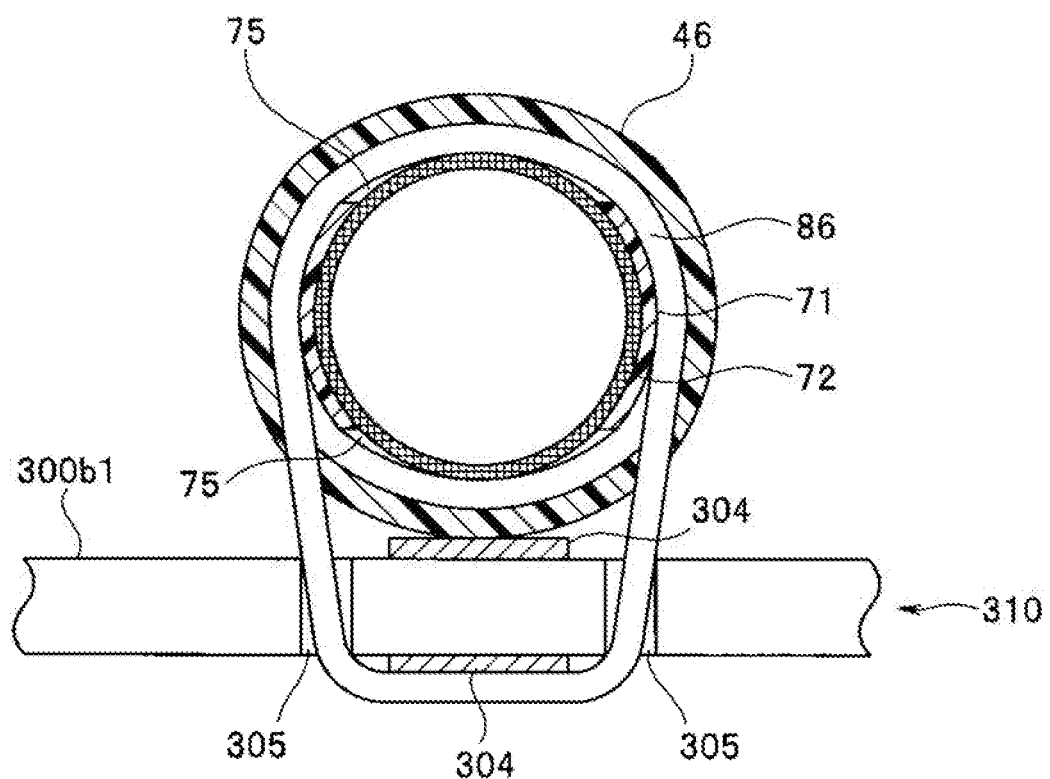
FIG. 23 is a cross-sectional view taken along line C3-C3 of FIG. 22 according to the third embodiment of the present disclosure.

Furthermore, as illustrated in FIGS. 22 and 23, a securing structure may be employed in which the end of the cable 70 is fixed to a connector board 310 by the binding thread 86. The connector board 310 has an edge connector portion 300a with an array of contacts 301 disposed thereon, as with the connector board 300, and a terminal portion 300b1 that includes an extension from the terminal portion 300b of the connector board 300 toward a proximal-end side thereof. The end of the cable 70 is fixed to the proximal-end side of the terminal portion 300b1.

Specifically, the connector board 310 has a plurality of lands 302 and 303 on the terminal portion 300b1 and a ground land 304 and through holes 305 on a proximal-end side of the lands 302 and 303 on the terminal portion 300b1. The through holes 305 are defined through the connector board 310. The cable 70 is disposed such that the shield layer 72 exposed through the openings 75 is positioned over the land 304 of the connector board 310. The cable 70 and the connector board 310 are bound together by the binding thread 86 that extends through the through holes 305 and secured together by soldering, electrically conductive adhesive bonding, or the like.

The cable 70 is thus fixed in position while the shield layer 72 of the cable 70 and the ground land 304 on the connector board 310 are electrically connected to each other. The securing structure securing for the cable end using the connector board 310 makes it possible to secure the cable 70 more firmly, effectively preventing the covering 71 from being displaced.

According to the third embodiment, as with the first and second embodiments, the covering is prevented from being displaced from the end of the cable due to loads on the cable that are imposed when the cable is bent, twisted, shifted, or otherwise disturbed. Furthermore, the distance that the securing portions 86a and 86b which secures the binding thread 86 project radially outwardly is reduced, preventing the cable from increasing in diameter. Moreover, the end of the covering and the securing portions are made positionally constant, making it possible to shorten the hardened length of the cable without impairing stability thereof.

Fourth Embodiment

Next, a fourth embodiment of the present disclosure will be described below. According to the fourth embodiment, a cable end is secured in place by a plate-shaped engaging member having hooks, instead of the binding thread 86 as a securing member according to the third embodiment.

Figure 24:
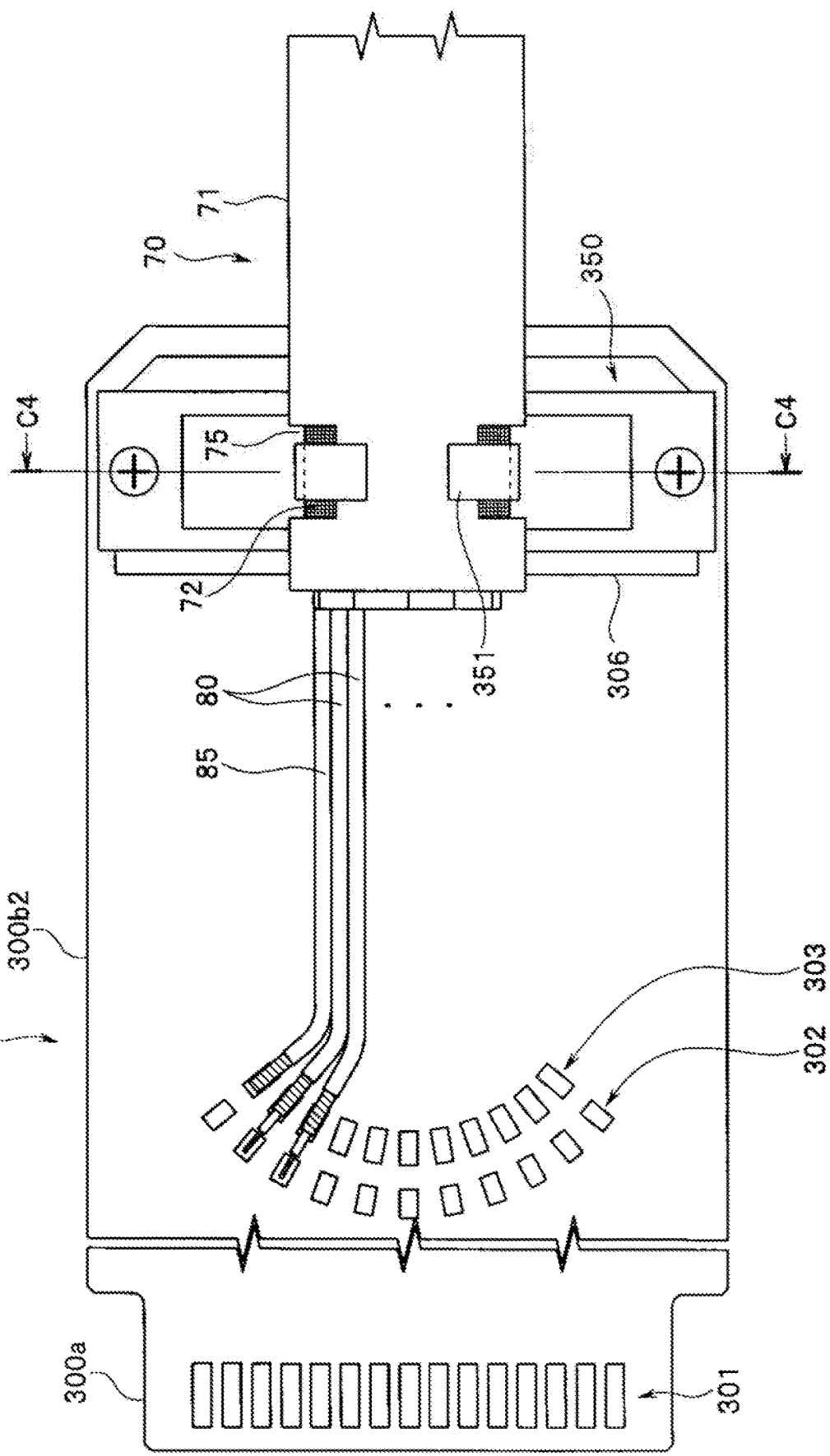
FIG. 24 is a view illustrating a securing structure at an end portion of a cable that is connected to an electric connector according to a fourth embodiment of the present disclosure.
Figure 25:
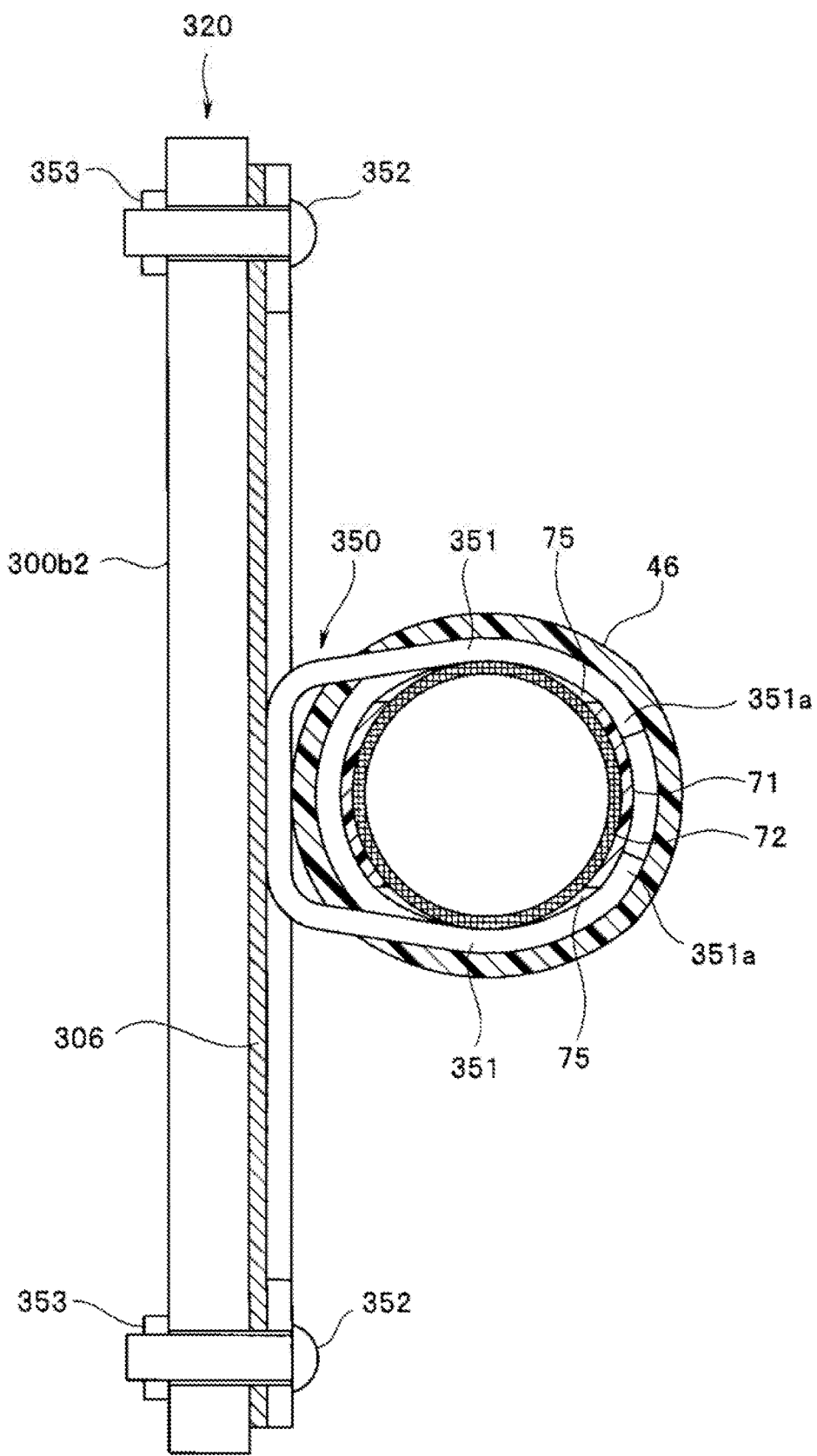
FIG. 25 is a cross-sectional view taken along line C4-C4 of FIG. 24 according to the fourth embodiment of the present disclosure.

As illustrated in FIGS. 24 and 25, a connector board 320 according to the fourth embodiment has an edge connector portion 300a with an array of contacts 301, similar to those on the connector board 300, disposed thereon and a terminal portion 300b2 that includes an extension from the terminal portion 300b of the connector board 300 toward a proximal-end side thereof. The terminal portion 302b of the connector board 320 has a ground land 306 on a proximal-end side of lands 302 and 303 on the terminal portion 300b2. The end of the cable 70 is secured in place by a plate-shaped engaging member 350 held against the ground land 306.

The engaging member 350 includes an electrically conductive, substantially rectangular plate-shaped member made of metal or the like, and has two slender engaging pieces 351 cut out of a central portion thereof in longitudinally confronting relation to each other. The engaging pieces 351 are bent upwardly and have distal-end portions formed as hooks 351a for securing the cable 70.

Specifically, the two engaging pieces 351 of the engaging member 350 are bent upwardly and raised, the cable 70 is placed between the two engaging pieces 351. The engaging pieces 351 are brought into contact with the shield layer 72 that is exposed through the openings 75 of the cable 70. Then, the hooks 351a are further bent to cause the engaging pieces 351 to press the cable 70.

The engaging pieces 351 now firmly engage the covering 71 and the shield layer 72 of the cable 70 in the vicinity of a joint portion of the cable 70 that is joined to the connector board 320. Since the engaging pieces 351 of the engaging member 350 engage the cable 70 such that they sink in the openings 75 of the cable 70, an electric connection is established between the engaging member 350 and the shield layer 72.

Next, the engaging member 350 is installed on the land 306 on the proximal-end side of the connector board 320 such that the lower surface of the engaging member 350 is held against the land 306. The engaging member 350 is thus secured to the connector board 320 while the engaging member 350 is being electrically connected to the shield layer 72 of the cable 70. FIGS. 24 and 25 illustrate an example in which the engaging member 350 has its both ends fastened and fixed to the connector board 320 by screws 352 and nuts 353. However, the engaging member 350 may be secured in position by being soldered to the land 306 of the connector board 320.

The engaging member 350 may be secured to the connector board 320 before the connector 70 is fixed to the engaging member 350. In FIGS. 24 and 25, the cable 70 is disposed in place such that the shield layer 72 in the openings 75 faces sides of the engaging pieces 351 and the hooks 351*a* on the distal ends thereof are bent in pressing relation to the covering 72. However, the cable 70 may not necessarily be limited to such an arrangement. The hooks 351*a* on the distal ends of the engaging pieces 351 may be disposed so as to press the shield layer 72.

According to the fourth embodiment, as with the embodiments described hereinbefore, the covering is prevented from being displaced from the end of the cable due to loads on the cable that are imposed when the cable is bent, twisted, shifted, or otherwise disturbed. In the fourth embodiment, furthermore, since the cable end is firmly secured in place simply by bending the engaging pieces 351 of the engaging member 350 in the absence of any thread-like securing member wound around the cable, the ease with which to work on the cable is increased.

In the above-described embodiments, the component includes the shield layer 72 and 92, 102, 252, and the sheath 73 and, leads 80 and 112 exposed from the covering 71 of the cable.

As noted hereinbefore, the binding thread 86 is wound around a covering 71 of a cable 70 in the position of an opening 75 defined in the covering 71. The wound portion of the binding thread 86 sinks from an outer surface of the covering 71 onto a shield layer 72 under the covering 71 in the opening 75. The binding thread 86 is tied into a knot as a securing portion 86*a* that secures the binding thread 86 in binding the covering 71 and is positioned on the shield layer 72 in the opening 75. Thereafter, the covering 71 is covered with a heat-shrinkable tube 46, securing the covering 71 and a sheath 73 and a plurality of leads 80 that are covered with the shield layer 72. The cable 70 is prevented from increasing in diameter due to the securing portion 86*a* that would otherwise project radially outwardly. The function of the binding thread 86 to find the covering 71 is prevented from being lowered due to the binding thread 86 that would otherwise tend to be displaced.

In sum, the disclosed technology is directed to an endoscopic apparatus comprises an endoscope having a cable connected to an electronic circuit part of the endoscope. The cable includes an elongated covering and an elongated component configured to be concentrically engaged with the elongated covering. A securing member is used to bind and to secure the elongated covering and the elongated component to one another. The elongated covering includes at least one recess formed on an outer circumferential area of the elongated covering on which the securing member binds and secures the elongated covering. The securing member has a securing portion that sinks in the at least one recess and secures the elongated covering and the elongated component that is exposed through the at least one recess.

The securing portion that secures the securing member is disposed in the at least one recess. The at least one recess is defined as a plurality of recesses at equal spaced intervals in the outer circumferential area. The securing member is wound into a plurality of turns around the elongated covering and at least one of the turns of the securing member sinks in the at least one recess. The securing member is an electrically conductive member and a part of the securing member that sinks in the at least one recess and is electrically connected to the metal member that is electrically connected to an electrically conductive frame of the endoscope. The elongated component that is exposed through the at least one recess of the elongated covering is a metal member. The at least one recess is defined by removing the elongated covering by applying a laser beam thereto. The cable is covered with a protective tube that covers at least the securing member. The electronic circuit part is a board on which a video signal processing circuit of the endoscope is mounted. The electronic circuit part is a switch disposed on a manipulator of the endoscope. The electronic circuit part is an electric connector that connects the endoscope to another apparatus in the endoscopic apparatus. The cable is secured by the securing member to a connector board having a plurality of contacts of the electric connector.

Another aspect of the disclosed technology is directed to an endoscopic apparatus comprises an endoscope having a cable connected to an electronic circuit part of the endoscope. The cable includes an elongated covering. An elongated component is configured to be concentrically engaged with the elongated covering. An engaging member is engaging the elongated covering and the elongated component to one another. The elongated covering includes at least one recess formed on an outer circumferential area of the elongated covering. The engaging member has a portion that sinks in the at least one recess and engages the elongated covering and the elongated component that is exposed through the at least one recess. The elongated component that is exposed through the at least one recess of the elongated covering includes a metal member.

A further aspect of the disclosed technology is directed to an endoscopic apparatus comprises an endoscope having a cable, a securing member and an electronic circuit. The cable includes a covering and a component that is connected to the electronic circuit. The component is exposed through the recess. The covering including a recess toward the component. The securing member binds and secures the covering and the component on the recess. The component is made of a metal. The securing member is an electrically conductive member and a part of the securing member is electrically connected to an electrically conductive frame of the endoscope. The cable is covered with a protective tube that covers the securing member.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one", "one or more" or the like; and adjectives such as "conventional", "traditional", "normal", "standard", "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more", "at least", "but not limited to" or other like phrases in some instances shall not be read to mean that the narrower case is intended or required in instances where such broadening phrases may be absent. Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:

1. An endoscope comprising:
   an electronic circuit part;
   a cable connected to the electronic circuit part, of wherein the cable comprises an elongated covering, an elongated shield layer and an elongated sheath, the shield layer being configured to be concentrically engaged with the elongated covering, the elongated covering includes at least one recess formed on an outer circumferential area of the elongated covering to expose the elongated shield layer through the at least one recess; and
   a securing member configured to secure the elongated covering to at least the elongated shield layer the securing member has a securing portion that sinks into the at least one recess and secures the elongated covering and the elongated shield layer that is exposed through the at least one recess,
   wherein the securing member is wound into a plurality of turns around the elongated covering, and at least one of the turns of the securing member sinks into the at least one recess.

2. The endoscope of claim 1, wherein the securing portion that secures the securing member is disposed in the at least one recess.

3. The endoscope of claim 1, wherein the at least one recess comprises a plurality of recesses circumferentially spaced at equal intervals in the outer circumferential area.

4. The endoscope of claim 1, wherein the elongated shield member that is exposed through the at least one recess of the elongated covering is at least partially formed of metal.

5. The endoscope of claim 4, further comprising an electrically conductive frame, wherein the securing member is formed of an electrically conductive material, a part of the securing member that sinks into the at least one recess is electrically connected to the elongated shield member, and the securing member is further electrically connected to the electrically conductive frame.

6. The endoscope of claim 4, wherein the at least one recess is formed by removing a portion of the elongated covering by applying a laser beam thereto.

7. The endoscope of claim 1, wherein the cable further comprises a protective tube that covers at least the securing member.

8. The endoscope of claim 1, wherein the electronic circuit part is a board on which a video signal processing circuit is mounted.

9. The endoscope of claim 1, further comprising a manipulator, wherein the electronic circuit part is a switch disposed on the manipulator.

10. The endoscope of claim 1, wherein the electronic circuit part is an electric connector that connects to another apparatus in an endoscopic apparatus.

11. The endoscope of claim 10, wherein the cable is secured by the securing member to a connector board having a plurality of contacts of the electric connector.

12. The endoscope of claim 1, wherein
    the securing member comprises an engaging member configured to engage the elongated covering, and at least the elongated shield layer, and the securing portion comprises an engaging portion that sinks into the at least one recess and engages the elongated covering and the elongated shield layer that is exposed through the at least one recess.

13. The endoscope of claim 12, wherein the elongated shield member that is exposed through the at least one recess of the elongated covering is at least partially formed of metal.

14. An insertion section for use with an endoscope, the insertion section comprising:
    an electronic circuit part;
    a cable connected to the electronic circuit part, wherein the cable comprises an elongated covering, an elongated shield layer and an elongated sheath, the shield layer being configured to be concentrically engaged with the elongated covering, the elongated covering includes at least one recess formed on an outer circumferential area of the elongated covering to expose the elongated shield layer through the at least one recess; and
    a securing member configured to secure the elongated covering to at least the elongated shield layer, the securing member has a securing portion that sinks into the at least one recess and secures the elongated covering and the elongated shield layer that is exposed through the at least one recess, wherein the securing member is wound into a plurality of turns around the elongated covering, and at least one of the turns of the securing member sinks into the at least one recess.

15. An image capturing unit comprising:

an electronic circuit part having a video processing circuit;

a cable connected to the electronic circuit part, wherein the cable comprises an elongated covering, an elongated shield layer and an elongated sheath, the shield layer being configured to be concentrically engaged with the elongated covering, the elongated covering includes at least one recess formed on an outer circumferential area of the elongated covering to expose the elongated shield layer through the at least one recess; and a securing member configured to secure the elongated covering to at least the elongated shield layer, the securing member has a securing portion that sinks into the at least one recess and secures the elongated covering and the elongated shield layer that is exposed through the at least one recess, wherein the securing member is wound into a plurality of turns around the elongated covering, and at least one of the turns of the securing member sinks into the at least one recess.

16. The endoscope of claim 15, further comprising an electrically conductive frame, wherein the elongated shield member that is exposed through the at least one recess of the elongated covering is at least partially formed of metal, the securing member is formed of an electrically conductive material, a part of the securing member that sinks into the at least one recess is electrically connected to the elongated shield member, the securing member is further electrically connected to the electrically conductive frame, and a protective tube covers at least the electrically conductive frame and the securing member.

* * * * *